(12) United States Patent
Chappa et al.

(10) Patent No.: US 8,927,000 B2
(45) Date of Patent: Jan. 6, 2015

(54) LIPID COATING FOR MEDICAL DEVICES DELIVERING BIOACTIVE AGENT

(75) Inventors: Ralph A. Chappa, Ham Lake, MN (US); Emily R. Rolfes Meyering, Eden Prairie, MN (US)

(73) Assignee: SurModics, Inc., Eden Prairie, MN (US)

( * ) Notice: Subject to any disclaimer, the term of this patent is extended or adjusted under 35 U.S.C. 154(b) by 551 days.

(21) Appl. No.: 13/173,143

(22) Filed: Jun. 30, 2011

(65) Prior Publication Data
US 2012/0165786 A1 Jun. 28, 2012

Related U.S. Application Data

(60) Provisional application No. 61/360,212, filed on Jun. 30, 2010.

(51) Int. Cl.
| A61L 29/06 | (2006.01) |
| A61M 25/10 | (2013.01) |
| A61L 29/08 | (2006.01) |
| A61L 29/16 | (2006.01) |
| A61L 29/04 | (2006.01) |
| A61L 29/14 | (2006.01) |

(52) U.S. Cl.
CPC .............. *A61L 29/085* (2013.01); *A61L 29/16* (2013.01); *A61L 29/044* (2013.01); *A61L 29/14* (2013.01); *A61M 2025/105* (2013.01); *A61L 29/145* (2013.01)
USPC ........................ 424/422; 604/915; 604/103.02

(58) Field of Classification Search
CPC ..................................................... A61M 25/10
USPC .............................. 424/422; 604/915, 103.02
See application file for complete search history.

(56) References Cited

U.S. PATENT DOCUMENTS

| 4,195,637 A | 4/1980 | Grüntzig et al. |
| 4,490,421 A | 12/1984 | Levy |
| 5,041,089 A | 8/1991 | Mueller et al. |
| 5,087,246 A | 2/1992 | Smith |
| 5,102,402 A | 4/1992 | Dror et al. |
| 5,304,121 A | 4/1994 | Sahatjian |
| 5,318,587 A | 6/1994 | Davey |
| 5,382,234 A | 1/1995 | Cornelius et al. |
| 5,414,075 A | 5/1995 | Swan et al. |
| 5,556,383 A | 9/1996 | Wang et al. |
| 5,571,089 A | 11/1996 | Crocker |

(Continued)

FOREIGN PATENT DOCUMENTS

| EP | 1 430 917 A1 | 6/2004 |
| EP | 1 834 636 | 9/2007 |

(Continued)

OTHER PUBLICATIONS

International Search Report and Written Opinion mailed Sep. 14, 2011.

*Primary Examiner* — Gollamudi Kishore
(74) *Attorney, Agent, or Firm* — Kagan Binder, PLLC

(57) ABSTRACT

The present invention relates compositions for delivering therapeutic agents from a medical device including an expandable and collapsible structure and methods employing them. A lipid coating including one or more fatty acids increases the amount of therapeutic agent released from the device at the delivery site. The therapeutic agent can be in a matrix including a hydrophilic polymer or an amphiphilic polymer. Release and adhesion coatings can also facilitate delivery of therapeutic agent.

17 Claims, 3 Drawing Sheets

(56) References Cited

U.S. PATENT DOCUMENTS

| | | |
|---|---|---|
| 5,674,192 A | 10/1997 | Sahatjian et al. |
| 5,776,101 A | 7/1998 | Goy |
| 5,807,331 A | 9/1998 | Den Heijer et al. |
| 5,882,336 A | 3/1999 | Janacek |
| 5,954,706 A * | 9/1999 | Sahatjian ............... 604/509 |
| 6,007,833 A | 12/1999 | Chudzik et al. |
| 6,129,705 A | 10/2000 | Grantz |
| 6,143,037 A | 11/2000 | Goldstein et al. |
| 6,168,748 B1 | 1/2001 | Wang et al. |
| 6,210,364 B1 | 4/2001 | Anderson et al. |
| 6,278,018 B1 | 8/2001 | Swan |
| 6,303,148 B1 | 10/2001 | Hennink et al. |
| 6,328,710 B1 | 12/2001 | Wang et al. |
| 6,364,893 B1 | 4/2002 | Sahatjian et al. |
| 6,394,995 B1 | 5/2002 | Solar et al. |
| 6,450,989 B2 | 9/2002 | Dubrul et al. |
| 6,482,348 B1 | 11/2002 | Wang et al. |
| 6,517,515 B1 | 2/2003 | Eidenschink |
| 6,544,579 B1 | 4/2003 | Landon |
| 6,610,317 B2 | 8/2003 | Straub et al. |
| 6,623,504 B2 | 9/2003 | Vrba et al. |
| 6,638,246 B1 | 10/2003 | Naimark et al. |
| 6,673,053 B2 | 1/2004 | Wang et al. |
| 6,703,040 B2 | 3/2004 | Katsarava et al. |
| 6,896,842 B1 | 5/2005 | Hamilton et al. |
| 6,911,216 B1 * | 6/2005 | Roth et al. ............... 424/489 |
| 7,060,051 B2 | 6/2006 | Palasis |
| 7,163,523 B2 | 1/2007 | Devens, Jr. et al. |
| 7,232,432 B2 | 6/2007 | Fulton, III et al. |
| RE40,359 E | 6/2008 | Katsarava et al. |
| 7,638,344 B2 | 12/2009 | Slager et al. |
| 2003/0064965 A1 | 4/2003 | Richter |
| 2003/0129130 A1 | 7/2003 | Guire et al. |
| 2005/0220843 A1 | 10/2005 | DeWitt et al. |
| 2005/0244459 A1 | 11/2005 | DeWitt et al. |
| 2005/0255142 A1 | 11/2005 | Chudzik et al. |
| 2006/0018948 A1 | 1/2006 | Guire et al. |
| 2006/0030669 A1 | 2/2006 | Taton et al. |
| 2007/0218102 A1 | 9/2007 | Chudzik et al. |
| 2007/0224247 A1 | 9/2007 | Chudzik et al. |
| 2007/0260054 A1 | 11/2007 | Chudzik |
| 2008/0015500 A1 | 1/2008 | Herweck et al. |
| 2008/0255509 A1 * | 10/2008 | Wang ............... 604/103.02 |
| 2009/0028956 A1 | 1/2009 | Slager et al. |
| 2009/0047414 A1 | 2/2009 | Corbeil et al. |
| 2009/0054837 A1 | 2/2009 | Von Holst et al. |
| 2009/0105687 A1 | 4/2009 | Deckman et al. |
| 2009/0246252 A1 | 10/2009 | Arps et al. |
| 2010/0040766 A1 | 2/2010 | Chappa et al. |
| 2010/0209472 A1 | 8/2010 | Wang |
| 2010/0226960 A1 * | 9/2010 | Chudzik et al. ............... 424/426 |

FOREIGN PATENT DOCUMENTS

| | | |
|---|---|---|
| WO | WO 03/000308 A1 | 1/2003 |
| WO | WO 2005/068533 | 7/2005 |
| WO | WO 2007/084418 | 7/2007 |
| WO | WO 2007/131802 A1 | 11/2007 |
| WO | WO 2010/136604 | 12/2010 |

* cited by examiner

LIPID COATING FOR MEDICAL DEVICES DELIVERING BIOACTIVE AGENT

CROSS-REFERENCE TO RELATED APPLICATIONS

This application claims benefit of Provisional Application No. 61/360,212, filed Jun. 30, 2010, which application is incorporated herein by reference.

FIELD OF THE INVENTION

The present invention relates to a lipid coating on an expandable and collapsible structure of a medical device and methods of making and using these coatings and devices. A coating including one or more lipids can increase the amount of therapeutic agent released from the device at the delivery site.

BACKGROUND OF THE INVENTION

The release of drugs from an implanted medical device has been shown to be beneficial for the function of devices and the treatment of various medical conditions. For example, delivery of a drug from the device surface can prevent cellular responses initiated by the presence of the implantable device. Also, drug released from the device can prevent conditions that would otherwise shorten the functional life of the device following implantation. Drug released from the device may also be directed at treating a diseased area of the body.

Some implantable devices simply have a drug applied to the device surface. Such preparations are generally undesirable because the drug can be easily removed from the surface during insertion. In addition, release of the drug is generally difficult to control following implantation.

Implantable medical devices having thin polymeric coatings containing therapeutic compounds have been described in the art and provide improvements for protecting and controlling the release of drug from the device surface. Some of these coatings are capable of releasing drugs to provide a local therapeutic effect in the vicinity of the implanted device. Such devices have been shown to be particularly valuable for the treatment of diseases of the cardiovascular system.

Drug-eluting stents can provide localized release of a therapeutic substance at the site of administration. Local administration of therapeutic agents via polymeric coatings on stents has shown favorable results in reducing restenosis. Several classes of polymer chemistries have been explored for use in drug-releasing coatings for stent as found in current art, some of which have been approved and are currently being used in medical procedures. Many of these chemistries are useful for delivering hydrophobic drugs.

For other medical applications, these polymer systems may not be ideal. For example, some applications involve the transient insertion of a medical device to a target tissue in the body. For the polymer systems described above, the rate of release of drug from such a polymer system may not be sufficient to provide a therapeutic amount of drug to the target tissue.

In addition, many of the drug delivery coating are made for devices with "static surfaces", that is, surfaces that do not increase in area. Typically, polymer systems that form durable coatings are suitable for these static surfaces. However, on surfaces that are non-static (e.g., elastic surfaces) such durable coatings may not always be appropriate.

SUMMARY OF THE INVENTION

The present invention relates to a lipid coating for medical devices including an expandable and collapsible structure and methods of making and employing them. A coating including one or more lipids increases the amount of therapeutic agent released from the device at the delivery site.

The present invention relates to a medical device including a lipid layer. This medical device can also include an expandable and collapsible structure and an agent coating on the expandable and collapsible structure. The agent coating includes a bioactive agent. The lipid coating is on the agent coating. The lipid coating can have a melting or softening point greater than room temperature and less than body temperature of the subject. This device is effective for delivering the bioactive agent to a site within a subject.

In an embodiment, the medical device is a balloon catheter. This balloon catheter includes a balloon and an agent coating on the balloon. The agent coating includes a bioactive agent. The device also includes a lipid coating on the agent coating. The lipid coating can have a melting or softening point greater than room temperature and less than body temperature of the subject. This balloon catheter is effective for delivering the bioactive agent to a site within a subject.

The present invention also includes a method of delivering a bioactive agent to a site in a subject, the method employing the present medical device. The method can include providing the present medical device and inserting the medical device into the subject. The method can also include expanding the expandable and collapsible structure at the site in the subject to contact a tissue at the site with the agent coating, the lipid coating, or both coatings to release bioactive agent to the tissue.

DETAILED DESCRIPTION

Figure 1:
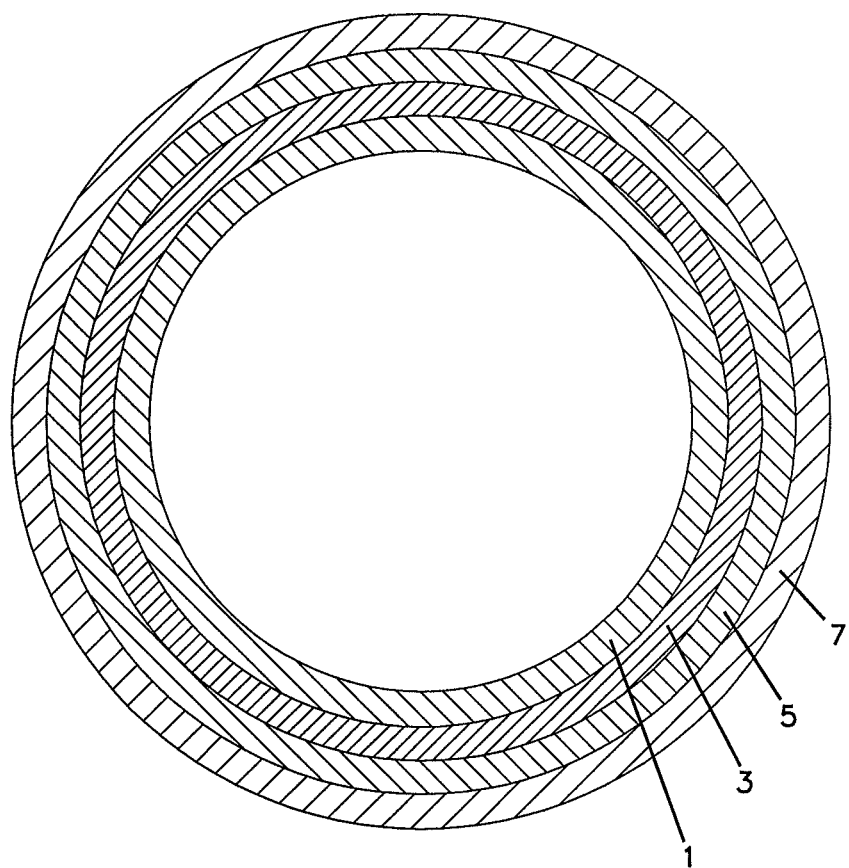
FIG. 1 schematically illustrates coatings on an expandable and collapsible structure.

The present invention relates to a medical device that delivers a bioactive agent to a site within a subject. The present invention also relates to methods of making and using the present device. At least a portion of the medical device can be inserted into the subject. The portion of the medical device that can be inserted into the subject includes an expandable and collapsible structure. In an embodiment, the expandable and collapsible structure is a balloon of a balloon catheter. On the expandable and collapsible structure, the device includes a coating including a bioactive agent (an agent coating). The device also includes a lipid coating on all or part of the coating including the bioactive agent.

The lipid coating can provide one or more of several advantageous characteristics to the medical device. The lipid coating can, for example: 1) protect an underlying coating that includes a bioactive agent (e.g., the agent coating); 2) serve as a lubricant (e.g., a sacrificial lubricant) as the device contacts a subject's tissue; 3) provide a deformable hydrophobic matrix that further enhances delivery to a hydrophobic tissue or surface thereof (e.g., the walls of a blood vessel); 4) provide a matrix that maintains the structural integrity of the assembled coatings and bioactive agent beneath (e.g., hold things together); or more than one of these characteristics.

In an embodiment, the lipid coating is solid (e.g., waxy) or semi-solid at room temperature and soft or liquid at the body temperature of a subject. For example, the lipid coating can be or include a lipid or mixture of lipids that is solid at room temperature and liquid at 37° C. and forms a coating that protects an underlying coating including a bioactive agent. A mixture of 50 wt-% oleic acid and 50 wt-% dodecanoic acid is such a coating composition. In an embodiment, the present lipid coating can increase the amount of bioactive agent that is delivered to a tissue after a balloon catheter is put through a tortuous path.

In an embodiment, the lipid coating is solid at room temperature but softens or melts (e.g., liquefies) when exposed to the subject's body temperature. In an embodiment, the barrier layer is solid at room temperature but softens or melts as the coated portion of the device makes its way through the subject to the site at which the bioactive agent is to be delivered (the delivery site). For example, the barrier layer can be made of or include a composition that has a melting or softening point that is greater than room temperature and less than the subject's body temperature. The softening or melting can occur as the coated portion of the device makes its way to the delivery site, the melting or softening can occur at the delivery site, or both. The softening, softened, melting, or melted lipid composition can leave the medical device, the portion of the medical device with the coating including the bioactive agent, or both as the coated portion of the device makes its way to the delivery site, at the delivery site, or both.

In an embodiment, the lipid coating can increase the amount of bioactive agent that is delivered to a desired location in a subject when the medical device is inserted into the subject. For example, the solid or semi-solid lipid coating can protect or isolate the coating including the bioactive agent during handling of the medical device outside the subject, as the coated portion of the device makes its way through the subject to the site at which the bioactive agent is to be delivered, or both. That is, the solid or semi-solid lipid coating can reduce the degree to which the coating including the bioactive agent is contacted by the atmosphere, by handling, by a guide catheter or other medical device, by tissue, by bodily fluids, or by a plurality thereof before the coated portion of the device arrives at the site at which the bioactive agent is to be delivered. This reduced contact can increase the amount of bioactive agent that is delivered at the desired site. Such a lipid coating has protected the underlying agent coating.

In an embodiment, the lipid coating increases the ease or reduces the resistance with which the medical device makes its way to the delivery site, for example, through a guide catheter. For example, the solid or semi-solid lipid coating can lubricate passage of the device as it is inserted into a guide catheter or other device, as the coated portion of the device makes its way through the guide catheter to the site at which the bioactive agent is to be delivered, or both. That is, the solid or semi-solid lipid coating can reduce the degree to which the coating including the bioactive agent contacts or rubs/abrades the guide catheter, the subject's tissue, bodily fluids, or both before the coated portion of the device arrives or is situated at the site at which the bioactive agent is to be delivered. The solid or semi-solid lipid coating can reduce friction from the device or the underlying coatings contacting a guide catheter, tissue, or fluid. Such lubricating can result in an increase the amount of bioactive agent that is delivered at the desired site. As the medical device makes its way to the delivery site, the lipid coating may be removed from the device as it lubricates. That is, the lipid coating can be a sacrificial lubricant.

In an embodiment, the lipid coating contacts the bioactive agent and the subject's tissue and aids in delivery of the agent to the tissue. The subject's tissue can have a degree of hydrophobicity that makes it more like the lipid coating composition than bodily fluids or the matrix making up the agent coating. The hydrophobicity of the lipid coating can aid absorption or adsorption of the bioactive agent into or onto the subject's tissue. In an embodiment, the bioactive agent may be in (e.g., dissolved or dispersed in) the lipid composition when it is at the delivery site. The lipid coating can adhere to the subject's tissue and also adhere bioactive agent (e.g., in the form of microparticles) to the subject's tissue. Such absorption, adsorption, or adhesion can result in an increase the amount of bioactive agent that is delivered at the desired site.

In an embodiment, the lipid coating increases the structural integrity of the coatings and bioactive agent on the device. For example, a solid or semisolid lipid coating can prevent or reduce the incidence of microparticles or portions of microparticles of active agent becoming dislodged from the device as it makes its way to the delivery site or as it is handled by medical personnel. The lipid coating can be viewed, for example, as a viscous matrix or an adhesive matrix that holds together these various coatings and particles as the medical device makes its way through a tortuous path to the delivery site. The lipid coating can be viewed, for example, as a viscous matrix or an adhesive matrix that holds together these various coatings and particles as the medical device contacts vessel walls or other tissue as it makes its way to the delivery site. As the medical device makes its way through the subject to the delivery site, the lipid coating may be removed from the device as it protects. That is, the lipid coating can serve as a sacrificial protectant.

A medical device including the present lipid coating can include a structure (e.g., a substrate) on which is disposed a coating (e.g., an agent coating) including a bioactive agent. The agent coating can be merely bioactive agent that has been deposited upon or adhered to the substrate. The agent coating can be a polymer matrix containing or immobilizing the bioactive agent. The lipid coating can be "on" the agent coating. That is, the lipid coating can be applied to or contacting the agent coating and between the agent coating and the environs of the medical device. The lipid coating can be on all or part of the agent coating.

In an embodiment, a major portion of the lipid coating is gone from the portion of the medical device bearing the coating including the bioactive agent when it arrives at the delivery site. That is, when the portion of the medical device with the coating including the bioactive agent arrives at the delivery site there remains an insufficient amount of the lipid coating composition to separate bioactive agent from the subject's tissue. In an embodiment, a major portion of the lipid coating is gone from the portion of the medical device with the coating including the bioactive agent when the bioactive agent is delivered to the subject's tissue at the delivery site. That is, for and during delivery of the bioactive agent there remains an insufficient amount of the lipid coating composition to separate the bioactive agent from the tissue. With a substantial portion of the lipid coating composition removed from the coating including the bioactive agent, the bioactive agent can be released from the coating and transferred to or taken up by (or both) the tissue at the delivery site.

In an embodiment, expanding the coated portion of the medical device increases the surface area of this portion of the device and decreases the thickness of (i.e., thins) the coating of the softened or melted lipid coating composition. It is possible that the decreased thickness or thinning of the lipid coating composition is sufficient for allowing release of the bioactive agent from the medical device. In an embodiment, after the decrease in thickness (e.g., thinning) and the removal of lipid coating composition from the medical device effective amounts of bioactive agent can be released from the medical device. For example, the thinned lipid coating composition may to some extent absorb or adsorb into or onto the tissue. In an embodiment, the thinned lipid coating composition includes bioactive agent, which also absorbs into or adsorbs onto the tissue. For example, the thinned lipid coating composition may adhere to the tissue. In an embodiment, the thinned lipid coating composition can adhere bioactive agent to the tissue. In an embodiment, the decrease in thickness upon expanding effectively removes the lipid coating composition from the expandable and collapsible structure.

In an embodiment of the present medical device, release of effective amounts of the bioactive agent from the medical device takes place in seconds to minutes, for example, 5 seconds to 2 minutes or 10 seconds to 1 minute.

FIG. 1 schematically illustrates embodiments of coatings 3, 5, and 7 on an expandable and collapsible structure 1. The coatings include optional release coating 3, an embodiment of agent coating 5, and an embodiment of lipid coating 7. Optional release coating 3, in this embodiment, is between the expandable and collapsible structure 1 and agent coating 5. Optional release coating 3 need not occupy the entire region between agent coating 5 and expandable and collapsible structure 1. Lipid coating 7 need not cover all of agent coating 5.

The Lipid Composition

The present lipid composition can include a lipid or mixture of lipids. The lipid or mixture of lipids can, for example, be solid (e.g., waxy or paste-like) or semi-solid at room temperature and soft or liquid at the body temperature of a subject.

In an embodiment, the lipid composition includes a lipid with a melting point at or above 40° C. and a lipid with a melting point at or below 20° C. In an embodiment, the lipid composition includes a lipid with a melting point at or above 37° C. and a lipid with a melting point at or below 30° C. In an embodiment, the lipid composition includes a lipid with a melting point of about 35 to about 45° C. and a lipid with a melting point of about 0 to about 35° C.

Lipids that can be employed in the present lipid coating include: a marine oil, such as an oil from herring, menhaden, pilchard, sardine, whale, or a mixture thereof; soybean oil, cottonseed oil, corn oil, peanut oil, sunflower oil, safflower oil, olive oil, palm oil, or a mixture thereof; or mixtures thereof. The lipid composition can be a mixture of a lipid that is liquid at room temperature and a lipid that is solid at room temperature. A lipid that is liquid at room temperature is sold under the trade name High Oleic CV-65 canola oil (Cargill Inc., Minnetonka, Minn.). In an embodiment, the oils that are liquid at room temperature are not hydrogenated (e.g., neither partially hydrogenated nor fully hydrogenated). In an embodiment, the lipid that is solid at room temperature is an oil listed above that is partially or fully hydrogenated, for example, fully hydrogenated. A lipid that is liquid at room temperature is sold under the trade name STABLE FLAKE C® and is a cottonseed stearine product (C. & T. Refinery, Inc. of Richmond, Va.)

In certain embodiments, the lipid composition can include: an oil such as vegetable oil, flower oil, animal oil, marine oil (e.g., fish oil), tropical oil (e.g., coconut oil or palm oil), olive oil, peanut oil; lard, butterfat; a saturated fatty acid, for example, butanoic acid, hexanoic acid, octanoic acid, decanoic acid, dodecanoic acid, tetradecanoic acid, hexadecanoic acid, octadecanoic acid, or a mixture thereof; an unsaturated fatty acid, for example, octadecatrienoic acid, eicosanoic acid, eicosenoic acid, eicosatetraenoic acid, eicosapentaenoic acid, docosahexaenoic acid, palmitoleic acid, stearic acid, oleic acid, vaccenic acid, linoleic acid, alpha-linolenic acid, gamma-linolenic acid, behenic acid, erucic acid, lignoceric acid; a natural or synthetic phospholipids, for example, phosphatidylglycerol, phosphatidic acid, phosphatidylcholine; cardiolipin, phosphatidylethanolamine, phosphatidylserine, phosphatidylinositol, dimyristoylphosphatidylcholine, dioleoylphosphatidylcholine, dipalmitoylphosphatidylcholine, distearoylphosphatidylcholine; a mono-, di-, or triacylglycerol; or mixture thereof. Lard is rendered and clarified pork fat and melts around 86° F. (30° C.).

In certain embodiments, the present lipid composition can include one or more of a fat, a wax, a sterol, a phospholipid; a mono-; di-, or tri-glyceride; a fatty acyl, a glycerolipid, a glycerophospholipid, a sphingolipid (e.g., sphingomyelin), a saccharolipid, a polyketide, a sterol lipid, a prenol lipid, or a mixture thereof. Additional suitable lipids include a ceramide, a phosphosphingolipid, a glycosphingolipid, which can include fatty acid moieties that are saturated or mono-unsaturated with chain lengths from 16 to 26 carbon atoms.

The melting point of the present lipid composition can be determined by any one of a variety of art accepted methods. Suitable methods include the Mettler drop point test (see, e.g., ASTM D 3954). Briefly, in this test the sample to be measured is placed in a cup and heated at a given rate. The temperature at which a drop of molten material passes through a standard orifice is recorded. Other methods include the AOCS Method Cc 2-38 (the Wiley melting point), open capillary slip point, and the softening point tests.

Useful methods for making lipid compositions of that are or appear solid at room temperature and components of these compositions include those described in U.S. Pat. No. 6,544,579, which is incorporated herein by reference. The lipid composition can be cooled at ambient temperature or supercooled to provide the lipid coating.

In an embodiment, the lipid composition consists essentially of one or more lipids. In an embodiment, the lipid composition consists of one or more lipids. The lipid is generally not an active agent.

Fatty Acids

The present lipid composition can include one or more fatty acids, meaning free fatty acid not esterified or otherwise derivatized fatty acid. The fatty acid can include or be a salt of the carboxylic acid (e.g., a salt of the fatty acid). Suitable fatty acids include saturated and unsaturated fatty acids. Suitable unsaturated fatty acids include mono-unsaturated fatty acids and polyunsaturated fatty acids. In an embodiment, the fatty acid composition includes a mono-unsaturated fatty acid. In an embodiment, the fatty acid composition includes a saturated fatty acid. In an embodiment, the fatty acid composition includes a saturated fatty acid and a mono-unsaturated fatty acid.

Suitable saturated fatty acids include those including 6 to 28 carbon atoms. In an embodiment, the saturated fatty acid is of the formula $CH_3(CH_2)_n COOH$, where $4 \leq n \leq 18$. In certain embodiments, n is 4, 5, 6, 7, 8, 9, 10, 11, 12, 13, 14, 15, 16, 17, or 18. In certain embodiments, $6 \leq n \leq 18$, $8 \leq n \leq 16$, or $10 \leq n \leq 14$. In an embodiment, n is 10.

Suitable unsaturated fatty acids include those including 8 to 24 carbon atoms. In an embodiment, the unsaturated fatty acid is of the formula $CH_3(CH_2)_m C=CH(CH_2)_o COOH$, m and o are independently greater than or equal to 2 and less than or equal to 18. In certain embodiments, m is 2, 3, 4, 5, 6, 7, 8, 9, 10, 11, 12, 13, 14, 15, 16, 17, or 18. In certain embodiments, o is 2, 3, 4, 5, 6, 7, 8, 9, 10, 11, 12, 13, 14, 15, 16, 17, or 18. In certain embodiments, $4 \leq m \leq 18$, $6 \leq m \leq 14$, or $6 \leq m \leq 8$. In certain embodiments, $4 \leq o \leq 18$, $6 \leq o \leq 14$, or $6 \leq o \leq 8$. In an embodiment, m is 7, o is 11 and the double bond is cis. In an embodiment, the unsaturated fatty acid is of the formula $CH_2=CH(CH_2)_p COOH$ with $3 \leq p \leq 21$.

In an embodiment, the unsaturated fatty acid can be described by C:D where C is the number of carbon atoms and D is the number of double bonds. C can be 6 to 24 and D can be 2 to 6. C and D are integers. In an embodiment, D can be 1 and C can be 6 to 24. The locations and stereochemistry of the double bond can be specified also.

In an embodiment, the fatty acid composition includes a saturated fatty acid with a melting point at or above 30° C. and an unsaturated fatty acid with a melting point at or below 20° C. In an embodiment, the fatty acid composition includes a saturated fatty acid with a melting point at or above 35° C. and an unsaturated fatty acid with a melting point at or below 35° C. In an embodiment, the fatty acid composition includes a saturated fatty acid with a melting point of about 30 to about 45° C. and an unsaturated fatty acid with a melting point of about 0 to about 35° C.

In an embodiment, the lipid coating includes or is made of a plurality of fatty acids. The plurality of fatty acids can be two fatty acids. The lipid coating can be a fatty acid or mixture of (e.g. two) fatty acids. The fatty acid or fatty acids can be a composition that is or that makes up the barrier layer. The plurality of fatty acids can be a mixture of fatty acids that are solid at room temperature and soft or liquid at body temperature of the subject. The plurality of fatty acids can be a mixture of fatty acids having a softening temperature greater than room temperature and less than body temperature of the subject. The plurality of fatty acids can be a mixture of fatty acids having a melting point greater than room temperature and less than body temperature of the subject.

In an embodiment, the present invention relates to a medical device including an expandable and collapsible structure. This embodiment includes an agent coating on the expandable and collapsible structure, and the agent coating include a bioactive agent. This embodiment includes a lipid coating on the agent coating. In this embodiment, the lipid coating includes a mixture of two fatty acids. The mixture of fatty acids have a melting point greater than room temperature and less than body temperature of the subject. This device is effective for delivering the bioactive agent to a site within a subject.

In an embodiment, the present invention relates to a balloon catheter. The balloon catheter includes a balloon. This catheter includes an agent coating on the balloon, and the agent coating includes a bioactive agent. This catheter includes a lipid coating on the agent coating, and the lipid coating includes a fatty acid. This balloon catheter is effective for delivering the bioactive agent to a site within a subject.

Phospholipids

In an embodiment, the lipid composition includes a phospholipid. Suitable phospholipids include, for example, a phosphatidic acid, a phosphatidylcholine, a phosphatidylethanolamine, a phosphatidylserine, or mixture thereof.

Suitable phosphatidylcholines include, for example: 1,2-Didecanoyl-sn-glycero-3-phosphocholine (CAS no. 3436-44-0), 1,2-Dierucoyl-sn-glycero-3-phosphocholine (CAS no. 56649-39-9), 1,2-Dilinoleoyl-sn-glycero-3-phosphocholine (CAS no. 998-06-1), 1,2-Dilauroyl-sn-glycero-3-phosphocholine (CAS no. 18194-25-7), 1,2-Dimyristoyl-sn-glycero-3-phosphocholine (CAS no. 18194-24-6), 1,2-Dioleoyl-sn-glycero-3-phosphocholine (CAS no. 4235-95-4), 1,2-Dipalmitoyl-sn-glycero-3-phosphocholine (CAS no. 63-89-8), phosphatidylcholine purified from egg, phosphatidylcholine purified from soybean, lysophosphatidylcholine, 1-Myristoyl-2-palmitoyl-sn-glycero 3-phosphocholine, 1-Myristoyl-2-stearoyl-sn-glycero-3-phosphocholine, 1-Palmitoyl-2-myristoyl-sn-glycero-3-phosphocholine, 1-Palmitoyl-2-oleoyl-sn-glycero-3-phosphocholine (CAS no. 26853-31-6), 1,2-Distearoyl-sn-glycero-3-phosphocholine (CAS no. 816-94-4), 1-Palmitoyl-2-stearoyl-sn-glycero-3-phosphocholine, 1-Stearoyl-2-myristoyl-sn-glycero-3-phosphocholine, 1-Stearoyl-2-oleoyl-sn-glycero-3-phosphocholine, 1-Stearoyl-2-palmitoyl-sn-glycero-3-phosphocholine, or mixture thereof.

Suitable lysophosphatidylcholines include, for example: 1-Myristoyl-sn-glycero-3-phosphocholine (CAS no. 18194-24-6), 1-Palmitoyl-sn-glycero-3-phosphocholine (CAS no. 17364-16-8), 1-Stearoyl-sn-glycero-3-phosphocholine (CAS no. 19420-57-6), or mixture thereof.

Suitable phosphatidic acids include, for example: 1,2-Dierucoyl-sn-glycero-3-phosphate (Sodium Salt) (CAS no. 80724-31-8), 1,2-Dilauroyl-sn-glycero-3-phosphate (Sodium Salt), 1,2-Dimyristoyl-sn-glycero-3-phosphate (Sodium Salt) (CAS no. 80724-3), 1,2-Dioleoyl-sn-glycero-3-phosphate (Sodium Salt), 1,2-Dipalmitoyl-sn-glycero-3-phosphate (Sodium Salt) (CAS no. 71065-87-7), 1,2-Distearoyl-sn-glycero-3-phosphate (Sodium Salt) (CAS no. 108321-18-2), or mixture thereof.

Suitable phosphatidylethanolamines include, for example: 1,2-Dierucoyl-sn-glycero-3-phosphoethanolamine (CAS no. 988-07-2), 1,2-Dilauroyl-sn-glycero-3-phosphoethanolamine, 1,2-Dimyristoyl-sn-glycero-3-phosphoethanolamine (CAS no. 988-07-2), 1,2-Dioleoyl-sn-glycero-3-phosphoethanolamine, 1,2-Dipalmitoyl-sn-glycero-3-phosphoethanolamine (CAS no. 923-61-5), 1-Palmitoyl-2-oleoyl-sn-glycero-3-phosphoethanolamine, 1,2-Distearoyl-sn-glycero-3-phosphoethanolamine (CAS no. 1069-79-0), or mixture thereof.

Suitable phosphatidylserines include, for example: 1,2-Dilauroyl-sn-glycero-3-phosphoserine (Sodium Salt), 1,2-Dimyristoyl-sn-glycero-3-phosphoserine (Sodium Salt), 1,2-Dipalmitoyl-sn-glycero-3-phosphoserine (Sodium Salt), 1,2-Distearoyl-sn-glycero-3-phosphoserine (Sodium Salt), 1,2-Dioleoyl-sn-glycero-3-phosphoserine (Sodium Salt) (CAS no. 70614-14-1), or mixture thereof.

Methods Employing a Device Including the Present Lipid Coating

The present invention also includes a method for delivering a bioactive agent to a subject using the present device. The present method can include providing the present medical device. The method can also include inserting the medical device into a subject, and then expanding the expandable and collapsible structure in the subject. Upon or after expansion an effective amount of the bioactive agent is released to the subject's tissue.

Expanding the portion of the device brings the coating into contact with the subject's tissue. Contacting the subject's tissue with the coated portion of the device can remove lipid coating from the device. For example, the softened or melted (e.g., liquid) lipid coating composition may to some extent absorb or adsorb into or onto the tissue. In an embodiment, the softened or melted lipid coating composition includes bioactive agent, which also absorbs into or adsorbs onto the tissue. For example, the softened or melted (e.g., liquid) lipid coating composition may adhere to the tissue. In an embodiment, the softened or melted lipid coating composition can adhere bioactive agent to the tissue. The softened or melted lipid coating composition may be squeezed out of the decreasing space between the device and the tissue as the device expands. If the device rubs against a portion of the tissue near the delivery site, this may also remove softened or melted lipid coating composition from the device.

In an embodiment, the expanded portion of the medical device can be contracted or collapsed before the device is removed from the delivery site. The expanded portion can be elastic, like a balloon of a balloon catheter. Contracting or collapsing the expanded portion of the medical device can take place after an effective amount of the bioactive agent has been released at the delivery site. In certain embodiments, the expanded portion of the medical device can shrink, condense, constrict, deflate, or a plurality thereof in addition to or instead of contracting or collapsing.

In an embodiment, the present method delivers a bioactive agent to a site in a subject. This embodiment can include providing the present medical device. The device provided can include an expandable and collapsible structure and an agent coating on the expandable and collapsible structure. The agent coating can include a bioactive agent. The device can also include a lipid coating on the agent coating. The lipid coating can include a fatty acid. This method includes inserting the medical device into the subject. This method also includes expanding the expandable and collapsible structure at the site in the subject to contact a tissue at the site with the agent coating and the bioactive agent and to release bioactive agent to the tissue. This method can include releasing a portion of the agent coating at the site.

In an embodiment, the present method employs a device including an expandable and collapsible structure and an agent coating on the expandable and collapsible structure. This agent coating can include an amorphous bioactive agent and a matrix. The matrix can include an amphiphilic copolymer, a low molecular weight hydrophobic polymer, an organogel, or a deformable hydrogel. This device also includes an adhesion coating on the agent coating. The adhesion coating includes a cationic moiety or an adhesion protein.

In an embodiment, the present method employs a balloon catheter including one or more of the present coatings in balloon angioplasty. Balloon angioplasty can be carried out for the treatment of diseased arteries to reduce atherosclerotic stenosis or to recanalize occluded arteries. In such a procedure, obstructed intraluminal passages are reopened or dilated by inflation of the balloon at the occluded site. According to the invention, balloon catheter including one or more of the present coatings is inserted percutaneously into a luminal passage of a patient, such as an artery, vein, or airway. Once inserted, the balloon is advanced to the desired treatment site, where the balloon is inflated to dilate the luminal passage.

Coatings

The present medical device can include any of a variety of coatings including a bioactive agent. Numerous suitable coatings and polymers useful in such coatings are described herein. Certain embodiments suitable for release of bioactive agent from the expandable and collapsible structure can release effective amounts of the bioactive agent at the delivery site in seconds or minutes. The bioactive agent can be in an amorphous form incorporated into the coating or polymer matrix of the coating.

The coating including the bioactive agent can be on one or more portions of the expandable and collapsible structure, for example, on one or more portions of an exterior surface. The coating including the bioactive agent can cover the entire surface of the balloon portion of a balloon catheter. In that manner, when the balloon is expanded in situ, the bioactive agent can be transferred to the circumference of the lumen of the artery.

The coating including the bioactive agent can cover less than the entire surface of the expandable and collapsible structure, such as in a non-contiguous pattern. A "non-contiguous" coating refers to a coating material that does not cover the structure (e.g., the entire balloon surface), but rather formed at one or more portions of the surface. Non-contiguous coating patterns facilitate delamination of a biodegradable coated material from the expandable and collapsible surface when it is expanded. In some aspects, a non-contiguous biodegradable coating may experience little or no fracturing before it becomes delaminated from the surface. In other aspects, a non-contiguous biodegradable coatings can have a pattern that is easy to fracture, which facilitates delamination. In terms of inflation pressure, non-contiguous biodegradable coatings may require less force for coating delamination.

Biodegradable coatings having a non-contiguous pattern can be fomied directly on the expandable and collapsible surface of a balloon, or can be formed in association with another coated material, such as a flexible hydrogel layer. Non-contiguous patterns, such as dotted and striped patterns, can be formed using a spray coating apparatus.

The coating including the bioactive agent can be a flexible hydrogel matrix. The flexible hydrogel matrix can be made from a biostable hydrophilic polymer. The polymer can be covalently bonded to the expandable and collapsible structure, covalently bonded to other hydrophilic polymers in the matrix, or both. In some desired aspects, the biostable hydrophilic polymer is bonded to the substrate surface via reacted photogroups.

The coating including the bioactive agent can include a water-soluble polymer, for example, a water-soluble polymer such as poly(vinylpyrolidone). In some cases, the coating includes a polymer that is covalently bonded to the surface of expandable and collapsible structure via reacted photogroups. The coating can also be formed from a composition in which the water-soluble polymer is in macromer form.

In an embodiment, at least a portion of the coating including the bioactive agent is capable of becoming delaminated upon expansion of the expandable and collapsible structure in the subject. The delaminated biodegradable polymeric matrix with bioactive agent can, for example, adhere to the target tissue. Degradation of the delaminated polymeric matrix and release of the bioactive agent can occur at the target site. The biodegradable polymeric matrix can be used in association with the flexible hydrogel matrix. The flexible hydrogel matrix can be the release coating. The biodegradable polymeric matrix can include the bioactive agent.

In an embodiment, the bioactive agent can be embedded in and/or attached to a fracturable, biodegradable coating that is present on the expandable and collapsible structure. In a non-expanded state, the bioactive material is substantially or entirely entrapped in the coating, or adhered to a coated layer, or both. Upon expansion of the substrate, the coating fractures and delaminates from the expandable and collapsible surface. Therefore, the coating can have properties of rigidity and brittleness. At the target site, portions of the coating are transferred to tissue along with the entrapped bioactive agent. In some cases the portions of the transferred coating can adhere to the tissue and provide a barrier or skin to improve its immobilization. Along with degradation of the biodegradable coating materials, bioactive agent can be released to provide a therapeutic effect.

The present medical device can also include any of a variety of coatings that aid in delivering a bioactive agent. Such coatings include a release coating and an adhesion coating.

Numerous suitable coatings and polymers useful in such coatings are described in a herein.

In an embodiment, the present medical device includes a release coating. The release coating can be on the expandable and contractible structure and can promote release of the coating including the bioactive agent (the agent coating) from this structure at the delivery site. The release coating can be between the agent coating and the expandable and collapsible structure. The release coating can be configured to promote release of the agent coating at the site within the subject. For example, the release coating can swell and push against the drug containing coating. In an embodiment, it pushes against and fractures the drug containing coating. In an embodiment, the release coating includes or is made of a water swellable polymer that rapidly absorbs water. Upon exposure to blood, water wicks into the layer and reduces the adhesion between the release layer and the agent coating.

In an embodiment, the present medical device includes an adhesion coating. The adhesion coating can be on the expandable and contractible structure and can promote adhesion of the agent coating to the subject's tissue at the delivery site. For example, the adhesion coating can be on the agent coating. For example, adhesion components can be in the agent coating. The adhesion coating can include a cationic moiety or an adhesion protein. The adhesion protein can be or can include collagen, heparin, laminin, or mixture thereof. In an embodiment, the adhesion coating can provide adhesive material for binding to a lesion, such as a lesion in a blood vessel. Components of the lesion to which adhesion can occur include cells, collagen, cholesterol, lipoproteins, or calcifications.

The device can include a degradable coated layer present between the coating including the bioactive agent and the surface of the expandable and collapsible structure. For example, the degradable layer can be present as a base coat on the surface of the expandable and collapsible structure.

Coating Polymers

The coating can be formed from polymeric material (one or more polymers) that allows immobilization of the bioactive agent in a non-expanded state. The polymeric material can include one or more homopolymers, copolymers, combinations or blends thereof useful for forming the matrix. In an aspect, the polymeric material is used to form an flexible hydrogel matrix as the coating.

In some modes of preparation, a coating composition is formed that includes one or more matrix-forming polymer and bioactive agent. Generally, the coating material is chosen and used in a composition suitable for forming a matrix with the bioactive agent. In one mode of practice, a hydrophilic polymer is used to prepare an aqueous composition that also includes the bioactive agent. The bioactive agent can be water insoluble, meaning that it does not readily dissolve in water.

In other cases, bioactive agent is not included in a coating composition having the one or more matrix-forming polymer. In such a coating process, the bioactive agent is used in a subsequent coating step where they become associated with the coated polymeric matrix.

Generally, a coating composition includes an amount and type of polymeric material that provides suitable physical properties (such as elasticity and bioactive agent retention). In some aspects the amount of polymeric material used to form the matrix in the composition is at a concentration in the range of about 5 mg/mL to about 50 mg/mL, about 10 mg/mL to about 40 mg/mL, or about 10 mg/mL to about 20 mg/mL. In exemplary modes of practice the polymeric material is present in the coating composition at about 15 mg/mL.

The polymeric material can also include pendent photoreactive or polymerizable groups that can be activated to form a crosslinked matrix of polymer. The amount of polymer in the composition can also be chosen based on the level of derivatization with these groups.

One class of hydrophilic polymers useful as polymeric materials for matrix formation is synthetic hydrophilic polymers. Synthetic hydrophilic polymers that are biostable (i.e., that show no appreciable degradation in vivo) can be prepared from any suitable monomer including acrylic monomers, vinyl monomers, ether monomers, or combinations of any one or more of these types of monomers. Acrylic monomers include, for example, methacrylate, methyl methacrylate, hydroxyethyl methacrylate, hydroxyethyl acrylate, methacrylic acid, acrylic acid, glycerol acrylate, glycerol methacrylate, acrylamide, methacrylamide, dimethylacrylamide (DMA), and derivatives and/or mixtures of any of these. Vinyl monomers include, for example, vinyl acetate, vinylpyrrolidone, vinyl alcohol, and derivatives of any of these. Ether monomers include, for example, ethylene oxide, propylene oxide, butylene oxide, and derivatives of any of these.

Examples of polymers that can be formed from these monomers include poly(acrylamide), poly(methacrylamide), poly(vinylpyrrolidone), poly(acrylic acid), poly(ethylene glycol), poly(vinyl alcohol), and poly(HEMA). Examples of hydrophilic copolymers include, for example, methyl vinyl ether/maleic anhydride copolymers and vinyl pyrrolidone/(meth)acrylamide copolymers. Mixtures of homopolymers and/or copolymers can be used.

Examples of some acrylamide-based polymers, such as poly(N,N-dimethylacrylamide-co-aminopropylmethacrylamide) and poly(acrylamide-co-N,N-dimethylaminopropylmethacrylamide) are described in example 2 of U.S. Patent Pub. No. 2006/0030669 filed Sep. 17, 2004 (Taton et al.), the disclosure of which is incorporated herein by reference.

In some embodiments, the hydrophilic polymer is a vinyl pyrrolidone polymer, or a vinyl pyrrolidone/(meth)acrylamide copolymer such as poly(vinylpyrrolidone-co-methacrylamide). If a PVP copolymer is used, it can be a copolymer of vinylpyrrolidone and a monomer selected from the group of acrylamide monomers. Exemplary acrylamide monomers include (meth)acrylamide and (meth)acrylamide derivatives, such as alkyl(meth)acrylamide, as exemplified by dimethylacrylamide, and aminoalkyl(meth)acrylamide, as exemplified by aminopropylmethacrylamide and dimethylaminopropylmethacrylamide. For example, poly(vinylpyrrolidone-co-N,N-dimethylaminopropylmethacrylamide) is described in example 2 of U.S. Patent Pub. No. 2006/0030669 (Taton et al.).

In one embodiment, the polymers and copolymers as described are derivatized with one or more photoactivatable group(s). Exemplary photoreactive groups that can be pendent from biostable hydrophilic polymer include aryl ketones, such as acetophenone, benzophenone, anthraquinone, anthrone, quinone, and anthrone-like heterocycles. This provides a hydrophilic polymer having a pendent activatable photogroup that can be applied to the expandable and collapsible structure, and then treated with actinic radiation sufficient to activate the photogroups and cause covalent bonding to a target, such as the material of the expandable and collapsible structure. Use of photo-hydrophilic polymers can be used to provide a durable coating of a flexible hydrogel matrix, with the hydrophilic polymeric materials covalently bonded to the material of the expandable and collapsible structure.

A hydrophilic polymer having pendent photoreactive groups can be used to prepare the flexible hydrogel coating.

Methods of preparing hydrophilic polymers having photoreactive groups are known in the art. For example, methods for the preparation of photo-PVP are described in U.S. Pat. No. 5,414,075, the disclosure of which is incorporated herein by reference. Methods for the preparation of photo-polyacrylamide are described in U.S. Pat. No. 6,007,833, the disclosure of which is incorporated herein by reference.

In another embodiment, the polymers and copolymers as described are derivatized with one or more polymerizable group(s). Polymers with pendent polymerizable groups are commonly referred to macromers. The polymerizable group(s) can be present at the terminal portions (ends) of the polymeric strand or can be present along the length of the polymer. In one embodiment polymerizable groups are located randomly along the length of the polymer. Polymerizable groups can be activated form a crosslinked matrix in which the bioactive agent is immobilized.

Optionally, the coating can include a cross-linking agent. A crosslinking agent can promote the association of polymers in the coating, or the bonding of polymers to the coated surface. The choice of a particular crosslinking agent can depend on the ingredients of the coating composition.

Suitable crosslinking agents include two or more activatable groups, which can react with the polymers in the composition. Suitable activatable groups include photoreactive groups as described herein, like aryl ketones, such as acetophenone, benzophenone, anthraquinone, anthrone, quinone, and anthrone-like heterocycles.

The photoactivatable cross-linking agent can be ionic, and can have good solubility in an aqueous composition. Thus, in some embodiments, at least one ionic photoactivatable crosslinking agent is used to form the coating. The ionic crosslinking agent can include an acidic group or salt thereof, such as selected from sulfonic acids, carboxylic acids, phosphonic acids, salts thereof, and the like. Exemplary counter ions include alkali, alkaline earths metals, ammonium, protonated amines, and the like.

Exemplary ionic photoactivatable cross-linking agents include 4,5-bis(4-benzoylphenylmethyleneoxy)benzene-1,3-disulfonic acid or salt; 2,5-bis(4-benzoylphenylmethyleneoxy)benzene-1,4-disulfonic acid or salt; 2,5-bis(4-benzoylmethyleneoxy)benzene-1-sulfonic acid or salt; N,N-bis[2-(4-benzoylbenzyloxy)ethyl]-2-aminoethanesulfonic acid or salt, and the like. See U.S. Pat. No. 6,278,018, the disclosure of which is incorporated herein by reference.

Natural polymers can also be used to form the matrix. Natural polymers include polysaccharides, for example, polydextrans, carboxymethylcellulose, and hydroxymethylcellulose; glycosaminoglycans, for example, hyaluronic acid; polypeptides, for example, soluble proteins such as collagen, albumin, and avidin; and combinations of these natural polymers. Combinations of natural and synthetic polymers can also be used.

In one mode of practice, the bioactive agent includes a first polymer that has a lower Tg than a second polymer. The second polymer, which is harder, can reduce the rate of release of the bioactive agent from the matrix. For example, the Tg of a suitable first polymer such as PLGA is about 45° C., and the Tg of a suitable second polymer such as PLLA is about 55° C. In some aspects the difference between the Tg of the first and second polymer is about 5° C. or greater. In more specific aspects the difference between the Tg of the first and second polymer is about 10° C. or greater. In some aspects, the first and second polymers have Tgs of about 35° C. or greater. In more specific aspects the first and second polymers have Tgs in the range of about 35° C. to about 65° C.

Selection of the first and second polymers can also be based on other properties of the polymers such as molecular weight, solubility, and rheology.

In certain embodiments, the polymer matrix includes an amphiphilic copolymer, a low molecular weight hydrophobic polymer, an organogel, a deformable hydrogel, a plurality thereof, or a mixture thereof. In an embodiment, the coating including a bioactive agent includes or is made of an amphiphilic copolymer. Suitable amphiphilic copolymers include a lactide/glycolide/caprolatone/polyethylene glycol copolymer. Such a copolymer can include blocks of polyethylene glycol. Although not limiting to the present invention, it is believed that an amphiphilic copolymer includes hydrophobic domains that enhance solubility of hydrophobic drugs and hydrophilic domains absorb water allowing the coating to swell upon exposure to blood.

In an embodiment, the coating including a bioactive agent includes or is made of a hydrophobic polymer of low average molecular weight. Suitable low molecular weight hydrophobic polymers include a polylactide/glycolide/caprolactone copolymer.

In an embodiment, the agent coating includes one or more solvents and the bioactive agent. In an embodiment, the agent coating includes an organogel. In an embodiment, the agent coating includes a deformable hydrogel.

In an embodiment, the agent coating includes a lipid. Although not limiting to the present invention it is believed that the lipid can enhance adhesion and penetration of drug into tissue. Drug can be emulsified into a lipid carrier.

In an embodiment, the drug is dissolved or dispersed in a deformable polymer layer, e.g., a hydrophobic polymer, an organogel, or a deformable hydrogel. In an embodiment, such a coating can flow or escape from the balloon surface and conform or adhere to the tissue upon expansion of the balloon.

Biodegradable Polymer

The biodegradable polymer can include one or more (e.g., 1, 2, 3 or 4) specific biodegradable polymers, for use in forming an implant in vivo. Suitable polymers will be biodegradable and will be substantially soluble in the biocompatible solvent system. Specifically, the biodegradable polymer can have a solubility of at least about 50 g/L in the biocompatible solvent system, at 25° C. and 1 atm. In one embodiment, the biodegradable polymer will not include a polymer that is substantially insoluble in the biocompatible solvent system. In an embodiment, the biodegradable polymer will not include a biodegradable polymer that is substantially insoluble in water or bodily fluids.

Suitable specific classes of polymers include, e.g., polylactides, polyglycolides, polycaprolactones, polyanhydrides, polyamines, polyurethanes, polyesteramides, polyorthoesters, polydioxanones, polyacetals, polyketals, polycarbonates, polyorthocarbonates, polyphosphazenes, succinates, poly(malic acid), poly(amino acids), polyvinylpyrrolidone, polyethylene glycol, polyhydroxycellulose, polysaccharides, chitin, chitosan, and copolymers, block copolymers, multi-block co-polymers, multi-block co-polymers with polyethylene glycol (PEG), polyols, terpolymers and mixtures thereof.

In one embodiment, the biodegradable polymer is a thermoplastic polymer.

In one embodiment, the biodegradable polymer has a viscosity of at least about 100 cP at 37° C. In other embodiments, the biodegradable polymer has a viscosity of about 1,000 cP to about 30,000 cp at 37° C., about 5,000 cP to about 25,000 cp at 37° C., or about 10,000 cP to about 20,000 cp at 37° C.

In one embodiment, the biodegradable polymer is hydrophobic.

In one embodiment, the biodegradable polymer includes a block copolymer. In an embodiment, the biodegradable polymer is a polyethylene glycol (PEG) containing tri-block copolymer.

In one embodiment the polymer contains functional side groups.

The biodegradable polymer can be present in any suitable and effective amount, provided the biodegradable polymer is substantially soluble in the solvent system, and in combination with the solvent system will form an implant in vivo. In one embodiment, the biodegradable polymer is present in about 10 wt. % to about 40 wt. % of the formulation. In an embodiment, the biodegradable polymer is present in about 40 wt. % to about 90 wt. % of the formulation.

In one embodiment, the biodegradable polymer can include a poly(ether ester) multi-block copolymer, for example, that sold under the trade name SynBiosys™. In an embodiment, the biodegradable polymer can include a polyglycerol fatty acid ester. In an embodiment, the biodegradable polymer can include a PEG-PBT polymer. In an embodiment, the biodegradable polymer cane include a poly(ester-amide) polymer (PEA).

Poly(ether ester) Multi-Block Copolymers

One suitable class of biodegradable polymers useful in the present invention includes the poly(ether ester) multi-block copolymers. These multi-block copolymers are composed of various pre-polymer building blocks of different combinations of DL-lactide, glycolide, ε-caprolactone and polyethylene glycol. By varying the molecular composition, molecular weight (Mw 1200-6000) and ratio of the pre-polymer blocks, different functionalities can be introduced into the final polymer, which enables the creation of polymers with various physio-chemical properties. Both hydrophobic as well as hydrophilic/swellable polymers and slowly degrading as well as rapidly degrading polymers can be designed.

The poly(ether ester) multi-block copolymers can include a polymer as shown below (formula III):

extender, and which are specifically essentially completely amorphous under physiological conditions (moist environment, body temperature, which is approximately 37° C. for humans).

The resulting multi-block copolymers can specifically have a structure according to any of the formulae (1)-(3):

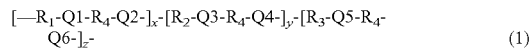  (1)

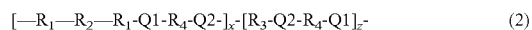  (2)

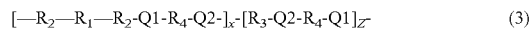  (3)

wherein:

$R_1$ and $R_2$ can be amorphous polyester, amorphous poly ether ester or amorphous polycarbonate; or an amorphous pre-polymer that is obtained from combined ester, ether and/or carbonate groups. $R_1$ and $R_2$ can contain polyether groups, which can result from the use of these compounds as a polymerization initiator, the polyether being amorphous or crystalline at room temperature. However, the polyether thus introduced will become amorphous at physiological conditions. $R_1$ and $R_2$ are derived from amorphous pre-polymers or blocks A and B, respectively, and $R_1$ and $R_2$ are not the same. $R_1$ and $R_2$ can contain a polyether group at the same time. In a specific embodiment, only one of them will contain a polyether group;

z is zero or a positive integer;

$R_3$ is a polyether, such as poly(ethylene glycol), and may be present (z≠0) or not (z=0). $R_3$ will become amorphous under physiological conditions;

$R_4$ is an aliphatic $C_2$-$C_8$ alkylene group, optionally substituted by a $C_1$-$C_{10}$ alkylene, the aliphatic group being linear or cyclic, wherein $R_4$ can specifically be a butylene, —$(CH_2)_4$-group, and the $C_1$-$C_{10}$ alkylene side group can contain protected S, N, P or O moieties;

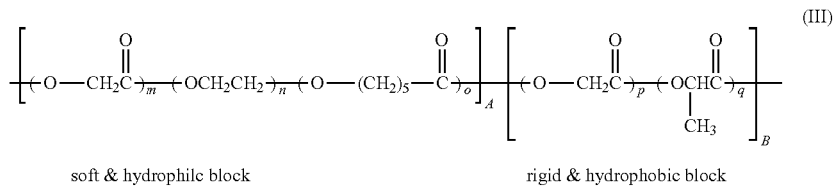

soft & hydrophilc block    rigid & hydrophobic block wherein, m and p are each independently glycolide;
n is polyethylene glycol, Mw 300-1000;
o is ε-caprolactone; and
q is DL-lactide.

Under physiological conditions, such poly(ether ester) multi-block copolymers can degrade completely via hydrolysis into non-toxic degradation products which are metabolized and/or excreted through the urinary pathway. Consequently, there can be no accumulation of biomaterials, thereby reducing the chance of long-term foreign body reactions.

Additional features and descriptions of the poly(ether ester) multi-block copolymers are provided, for example, in Published PCT Patent Application No. WO 2005/068533 and references cited therein. An overview is provided below.

The multi-block copolymers can specifically include two hydrolysable segments having a different composition, linked by a multifunctional, specifically an aliphatic chainx and y are both positive integers, which can both specifically be at least 1, whereas the sum of x and y (x+y) can specifically be at most 1000, more specifically at most 500, or at most 100. Q1-Q6 are linking units obtained by the reaction of the pre-polymers with the multifunctional chain-extender. Q1-Q6 are independently amine, urethane, amide, carbonate, ester or anhydride. The event that all linking groups Q are different being rare and not preferred.

Typically, one type of chain-extender can be used with three pre-polymers having the same end-groups, resulting in a copolymer of formula (1) with six similar linking groups. In case pre-polymers $R_1$ and $R_2$ are differently terminated, two types of groups Q will be present: e.g. Q1 and Q2 will be the same between two linked pre-polymer segments $R_1$, but Q1 and Q2 are different when $R_1$ and $R_2$ are linked. Obviously, when Q1 and Q2 are the same, it means that they are the same type of group but as mirror images of each other.

In copolymers of formula (2) and (3) the groups Q1 and Q2 are the same when two pre-polymers are present that are both terminated with the same end-group (which is usually hydroxyl) but are different when the pre-polymers are differently terminated (e.g. PEG which is diol terminated and a di-acid terminated 'tri-block' pre-polymer). In case of the tri-block pre-polymers ($R_1R_2R_1$ and $R_2R_1R_2$), the outer segments should be essentially free of PEG, because the coupling reaction by ring opening can otherwise not be carried out successfully. Only the inner block can be initiated by a PEG molecule.

The examples of formula (1), (2) and (3) show the result of the reaction with a di-functional chain-extender and di-functional pre-polymers.

With reference to formula (1) the polyesters can also be represented as multi-block or segmented copolymers having a structure (ab)n with alternating a and b segments or a structure (ab)r with a random distribution of segments a and b, wherein 'a' corresponds to the segment $R_1$ derived from pre-polymer (A) and 'b' corresponds to the segment $R_2$ derived from pre-polymer (B) (for z=0). In (ab)r, the a/b ratio (corresponding to x/y in formula (1)) may be unity or away from unity. The pre-polymers can be mixed in any desired amount and can be coupled by a multifunctional chain extender, viz. a compound having at least two functional groups by which it can be used to chemically link the pre-polymers. Specifically, this is a di-functional chain-extender. In case z≠0, then the presentation of a random distribution of all the segments can be given by (abc)r were three different pre-polymers (one being e.g. a polyethylene glycol) are randomly distributed in all possible ratio's. The alternating distribution is given by (abc)n. In this particular case, alternating means that two equally terminated pre-polymers (either a and c or b and c) are alternated with a differently terminated pre-polymer b or a, respectively, in an equivalent amount (a+c=b or b+c=a). Those according to formula (2) or (3) have a structure (aba)n and (bab)n wherein the aba and bab 'triblock' pre-polymers are chain-extended with a di-functional molecule.

The method to obtain a copolymer with a random distribution of a and b (and optionally c) is far more advantageous than when the segments are alternating in the copolymer such as in (ab)n with the ratio of pre-polymers a and b being 1. The composition of the copolymer can then only be determined by adjusting the pre-polymer lengths. In general, the a and b segment lengths in (ab)n alternating copolymers are smaller than blocks in block-copolymers with structures ABA or AB.

The pre-polymers of which the a and b (and optionally c) segments are formed in (ab)r, (abc)r, (ab)n and (abc)n are linked by the di-functional chain-extender. This chain-extender can specifically be a diisocyanate chain-extender, but can also be a diacid or diol compound. In case all pre-polymers contain hydroxyl end-groups, the linking units will be urethane groups. In case (one of) the pre-polymers are carboxylic acid terminated, the linking units are amide groups. Multi-block copolymers with structure (ab)r and (abc)r can also be prepared by reaction of di-carboxylic acid terminated pre-polymers with a diol chain extender or vice versa (diol terminated pre-polymer with diacid chain-extender) using a coupling agent such as DCC (dicyclohexyl carbodiimide) forming ester linkages. In (aba)n and (bab)n the aba and bab pre-polymers are also specifically linked by an aliphatic di-functional chain-extender, more specifically, a diisocyanate chain-extender.

The term "randomly segmented" copolymers refers to copolymers that have a random distribution (i.e. not alternating) of the segments a and b: (ab)r or a, b and c: (abc)r.

PEG-PBT Polymers

One suitable class of biodegradable polymers useful in the present invention include the poly(ether ester) multiblock copolymers based on poly(ethylene glycol) (PEG) and poly (butylene terephthalate) (PBT), that can be described by the following general formula IV:

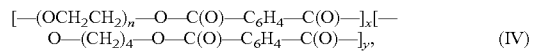

(IV)

wherein,

—$C_6H_4$— designates the divalent aromatic ring residue from each esterified molecule of terephthalic acid, n represents the number of ethylene oxide units in each hydrophilic PEG block, x represents the number of hydrophilic blocks in the copolymer, and y represents the number of hydrophobic blocks in the copolymer.

In specific embodiments, n can be selected such that the molecular weight of the PEG block is between about 300 and about 4000. In specific embodiments, x and y can each be independently selected so that the multiblock copolymer contains from about 55% up to about 80% PEG by weight.

The block copolymer can be engineered to provide a wide array of physical characteristics (e.g., hydrophilicity, adherence, strength, malleability, degradability, durability, flexibility) and bioactive agent release characteristics (e.g., through controlled polymer degradation and swelling) by varying the values of n, x and y in the copolymer structure.

Polyester Amides

One suitable class of biodegradable polymers useful in the present invention includes the polyesteramide polymers having a subunit of the formula (V):

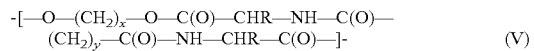

(V)

wherein, x is $C_2$-$C_{12}$, y is $C_2$-$C_{12}$, and

R is —$CH(CH_3)_2$, —$CH_2CH(CH_3)_2$, —$CH(CH_3)$ $CH_2CH_3$, —$CH_2(CH_2)_2CH_3$, —$CH_2C_6H_5$, $CH_2(CH_2)_2$ $SCH_3$ or part of an amino acid.

In specific embodiments, the $C_2$-$C_{12}$ can be ($C_2$-$C_{12}$) alkyl. In other specific embodiments, the $C_2$-$C_{12}$ can be ($C_2$-$C_{12}$) alkyl, optionally substituted.

Such polymers are described, for example, in U.S. Pat. No. 6,703,040. Polymers of this nature can be described with a nomenclature of x-aa-y, wherein "x" represents an alkyl diol with x carbon atoms, "aa" represents an amino acid such as leucine or phenylalanine, and y represents an alkyldicarboxylic acid with y carbon atoms, and wherein the polymer is a polymerization of the diol, the dicarboxylic acid, and the amino acid. An exemplary polymer of this type is 4-Leu-4.

Poly(Ester-Amide) Polymer (PEA)

One suitable class of biodegradable polymers useful in the present invention includes the poly(ester-amide) polymers. Such polymers can be prepared by polymerization of a diol, a dicarboxylic acid and an alpha-amino acid through ester and amide links in the form $(DACA)_n$. An example of a $(DACA)_n$ polymer is shown below in formula VI. Suitable amino acids include any natural or synthetic alpha-amino acid, specifically neutral amino acids.

Diols can be any aliphatic diol, including alkylene diols like HO—$(CH_2)_k$—OH (i.e. non-branched), branched diols (e.g., propylene glycol), cyclic diols (e.g. dianhydrohexitols and cyclohexanediol), or oligomeric diols based on ethylene glycol (e.g., diethylene glycol, triethylene glycol, tetraethylene glycol, or poly(ethylene glycol)s). Aromatic diols (e.g., bis-phenols) are less useful for these purposes since they are more toxic, and polymers based on them have rigid chains that are less likely to biodegrade.

Dicarboxylic acids can be any aliphatic dicarboxylic acid, such as α-omega-dicarboxylic acids (i.e., non-branched), branched dicarboxylic acids, cyclic dicarboxylic acids (e.g. cyclohexanedicarboxylic acid). Aromatic diacids (like phthalic acids, etc.) are less useful for these purposes since they are more toxic, and polymers based on them have rigid chain structure, exhibit poorer film-forming properties and have much lower tendency to biodegrade.

Specific PEA polymers have the formula VI:

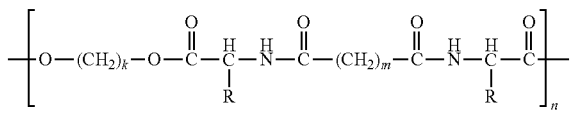

(VI)

wherein, k is 2-12 (e.g., 2, 3, 4, or 6);

m is 2-12 (e.g., 4 or 8); and

R is —CH(CH$_3$)$_2$, —CH$_2$CH(CH$_3$)$_2$, —CH(CH$_3$)CH$_2$CH$_3$, —CH$_2$(CH$_2$)$_2$CH$_3$, —CH$_2$(C$_6$H$_5$), or —CH$_2$(CH$_2$)SCH$_3$.

In specific embodiments, A is L-phenylalanine (Phe-PEA) and A is L-leucine (Leu-PEA). In specific embodiments, the ratio of Phe-PEA to Leu-PEA is from 10:1 to 1:1. In other specific embodiments, the ratio of Phe-PEA to Leu-PEA is from 5:1 to 2.5:1.

Additional features and descriptions of the poly(ester-amide) polymers (PEA) are provided, for example, in U.S. Re40,359, which is a reissue of U.S. Pat. No. 6,703,040.

Hydrophobic Derivatives of Natural Biodegradable Polysaccharides

One suitable class of biodegradable polymers useful in the present invention includes the hydrophobic derivatives of natural biodegradable polysaccharides, such as those sold under the trade name Eureka™ SOLO polymers. Hydrophobic derivatives of natural biodegradable polysaccharide refer to a natural biodegradable polysaccharide having one or more hydrophobic pendent groups attached to the polysaccharide. In many cases the hydrophobic derivative includes a plurality of groups that include hydrocarbon segments attached to the polysaccharide. When a plurality of groups including hydrocarbon segments are attached, they are collectively referred to as the "hydrophobic portion" of the hydrophobic derivative. The hydrophobic derivatives therefore include a hydrophobic portion and a polysaccharide portion.

The polysaccharide portion includes a natural biodegradable polysaccharide, which refers to a non-synthetic polysaccharide that is capable of being enzymatically degraded. Natural biodegradable polysaccharides include polysaccharide and/or polysaccharide derivatives that are obtained from natural sources, such as plants or animals. Natural biodegradable polysaccharides include any polysaccharide that has been processed or modified from a natural biodegradable polysaccharide (for example, maltodextrin is a natural biodegradable polysaccharide that is processed from starch). Exemplary natural biodegradable polysaccharides include maltodextrin, amylose, cyclodextrin, polyalditol, hyaluronic acid, dextran, heparin, chondroitin sulfate, demiatan sulfate, heparan sulfate, keratan sulfate, dextran, dextran sulfate, pentosan polysulfate, and chitosan. Specific polysaccharides are low molecular weight polymers that have little or no branching, such as those that are derived from and/or found in starch preparations, for example, maltodextrin, amylose, and cyclodextrin. Therefore, the natural biodegradable polysaccharide can be a substantially non-branched or completely non-branched poly(glucopyranose) polymer.

"Amylose" or "amylose polymer" refers to a linear polymer having repeating glucopyranose units that are joined by α-1,4 linkages. Some amylose polymers can have a very small amount of branching via α-1,6 linkages (about less than 0.5% of the linkages) but still demonstrate the same physical properties as linear (unbranched) amylose polymers do. Generally amylose polymers derived from plant sources have molecular weights of about 1×10$^6$ Da or less. Amylopectin, comparatively, is a branched polymer having repeating glucopyranose units that are joined by α-1,4 linkages to form linear portions and the linear portions are linked together via α-1,6 linkages. The branch point linkages are generally greater than 1% of the total linkages and typically 4%-5% of the total linkages. Generally amylopectin derived from plant sources have molecular weights of 1×10$^7$ Da or greater.

For example, in some aspects, starch preparations having a high amylose content, purified amylose, synthetically prepared amylose, or enriched amylose preparations can be used in the preparation of a hydrophobic derivative of amylose. In starch sources, amylose is typically present along with amylopectin, which is a branched polysaccharide. If a mixture of amylose and a higher molecular weight precursor is used (such as amylopectin), amylose can be present in the composition in an amount greater than the higher molecular weight precursor. For example, in some aspects, starch preparations having high amylose content, purified amylose, synthetically prepared amylose, or enriched amylose preparations can be used in the preparation of a hydrophobic derivative of amylose polymer. In some embodiments the composition includes a mixture of polysaccharides including amylose wherein the amylose content in the mixture of polysaccharides is 50% or greater, 60% or greater, 70% or greater, 80% or greater, or 85% or greater by weight. In other embodiments the composition includes a mixture of polysaccharides including amylose and amylopectin and wherein the amylopectin content in the mixture of polysaccharides is 30% or less, or 15% or less.

The amount of amylopectin present in a starch may also be reduced by treating the starch with amylopectinase, which cleaves α-1,6 linkages resulting in the debranching of amylopectin into amylose.

Steps may be performed before, during, and/or after the process of derivatizing the amylose polymer with a pendent group comprising a hydrocarbon segment to enrich the amount of amylose, or purify the amylose.

Amylose of particular molecular weights can be obtained commercially or can be prepared. For example, synthetic amyloses with average molecular masses of 70 kDa, 110 kDa, and 320 kDa, can be obtained from Nakano Vinegar Co., Ltd. (Aichi, Japan). The decision of using amylose of a particular size range may depend on factors such as the physical characteristics of the composition (e.g., viscosity), the desired rate of degradation of the implant, and the nature and amount of the active pharmaceutical ingredient (API).

Purified or enriched amylose preparations can be obtained commercially or can be prepared using standard biochemical techniques such as chromatography. In some aspects, high-amylose cornstarch can be used to prepare the hydrophobic derivative.

Maltodextrin is typically generated by hydrolyzing a starch slurry with heat-stable α-amylase at temperatures at 85-90° C. until the desired degree of hydrolysis is reached and then inactivating the α-amylase by a second heat treatment. The maltodextrin can be purified by filtration and then spray dried to a final product. Maltodextrins are typically characterized by their dextrose equivalent (DE) value, which is related to the degree of hydrolysis defined as: DE=MW dextrose/number-averaged MW starch hydrolysate X 100. Generally, maltodextrins are considered to have molecular weights that are less than amylose molecules.

A starch preparation that has been totally hydrolyzed to dextrose (glucose) has a DE of 100, whereas starch has a DE of about zero. A DE of greater than 0 but less than 100 characterizes the mean-average molecular weight of a starch hydrolysate, and maltodextrins are considered to have a DE of less than 20. Maltodextrins of various molecular weights, for example, in the range of about 500 Da to 5000 Da are commercially available (for example, from CarboMer, San Diego, Calif.).

Another contemplated class of natural biodegradable polysaccharides is natural biodegradable non-reducing polysaccharides. A non-reducing polysaccharide can provide an inert matrix thereby improving the stability of active pharmaceutical ingredients (APIs), such as proteins and enzymes. A non-reducing polysaccharide refers to a polymer of non-reducing disaccharides (two monosaccharides linked through their anomeric centers) such as trehalose (α-D-glucopyranosyl α-D-glucopyranoside) and sucrose (β-D-fructofuranosyl α-D-glucopyranoside). An exemplary non-reducing polysaccharide includes polyalditol which is available from GPC (Muscatine, Iowa). In another aspect, the polysaccharide is a glucopyranosyl polymer, such as a polymer that includes repeating (1→3)O-β-D-glucopyranosyl units.

Dextran is an α-D-1,6-glucose-linked glucan with sidechains 1-3 linked to the backbone units of the dextran biopolymer. Dextran includes hydroxyl groups at the 2, 3, and 4 positions on the glucopyranose monomeric units. Dextran can be obtained from fermentation of sucrose-containing media by *Leuconostoc mesenteroides* B512F.

Dextran can be obtained in low molecular weight preparations. Enzymes (dextranases) from molds such as *Penicillium* and *Verticillium* have been shown to degrade dextran. Similarly many bacteria produce extracellular dextranases that split dextran into low molecular weight sugars.

Chondroitin sulfate includes the repeating disaccharide units of D-galactosamine and D-glucuronic acid, and typically contains between 15 to 150 of these repeating units. Chondroitinase AC cleaves chondroitin sulfates A and C, and chondroitin.

Hyaluronic acid (HA) is a naturally derived linear polymer that includes alternating β-1,4-glucuronic acid and β-1,3-N-acetyl-D-glucosamine units. HA is the principal glycosaminoglycan in connective tissue fluids. HA can be fragmented in the presence of hyaluronidase.

In many aspects the polysaccharide portion and the hydrophobic portion include the predominant portion of the hydrophobic derivative of the natural biodegradable polysaccharide. Based on a weight percentage, the polysaccharide portion can be about 25% wt of the hydrophobic derivative or greater, in the range of about 25% to about 75%, in the range of about 30% to about 70%, in the range of about 35% to about 65%, in the range of about 40% to about 60%, or in the range of about 45% to about 55%. Likewise, based on a weight percentage of the overall hydrophobic derivative, the hydrophobic portion can be about 25% wt of the hydrophobic derivative or greater, in the range of about 25% to about 75%, in the range of about 30% to about 70%, in the range of about 35% to about 65%, in the range of about 40% to about 60%, or in the range of about 45% to about 55%. In exemplary aspects, the hydrophobic derivative has approximately 50% of its weight attributable to the polysaccharide portion, and approximately 50% of its weight attributable to its hydrophobic portion.

The hydrophobic derivative has the properties of being insoluble in water. The term for insolubility is a standard term used in the art, and meaning 1 part solute per 10,000 parts or greater solvent. (see, for example, Remington: The Science and Practice of Pharmacy, 20th ed. (2000), Lippincott Williams & Wilkins, Baltimore Md.).

A hydrophobic derivative can be prepared by associating one or more hydrophobic compound(s) with a natural biodegradable polysaccharide polymer. Methods for preparing hydrophobic derivatives of natural biodegradable polysaccharides are described herein.

The hydrophobic derivatives of the natural biodegradable polysaccharides specifically have an average molecular weight of up to about 1,000,000 Da, up to about 300,000 Da or up to about 100,000 Da. Use of these molecular weight derivatives can provide implants with desirable physical and drug-releasing properties. In some aspects the hydrophobic derivatives have a molecular weight of about 250,000 Da or less, about 100,000 Da or less, about 50,000 Da or less, or 25,000 Da or less. Particularly specific size ranges for the natural biodegradable polysaccharides are in the range of about 2,000 Da to about 20,000 Da, or about 4,000 Da to about 10,000 Da.

The molecular weight of the polymer is more precisely defined as "weight average molecular weight" or $M_w$. $M_w$ is an absolute method of measuring molecular weight and is particularly useful for measuring the molecular weight of a polymer (preparation). Polymer preparations typically include polymers that individually have minor variations in molecular weight. Polymers are molecules that have a relatively high molecular weight and such minor variations within the polymer preparation do not affect the overall properties of the polymer preparation. The $M_w$ can be measured using common techniques, such as light scattering or ultracentrifugation. Discussion of $M_w$ and other terms used to define the molecular weight of polymer preparations can be found in, for example, Allcock, H. R. and Lampe, F. W. (1990) *Contemporary Polymer Chemistry*; pg 271.

The addition of hydrophobic portion will generally cause an increase in molecular weight of the polysaccharide from its underivatized, starting molecular weight. The amount increase in molecular weight can depend on one or more factors, including the type of polysaccharide derivatized, the level of derivation, and, for example, the type or types of groups attached to the polysaccharide to provide the hydrophobic portion.

In some aspects, the addition of hydrophobic portion causes an increase in molecular weight of the polysaccharide of about 20% or greater, about 50% or greater, about 75% or greater, about 100% or greater, or about 125%, the increase in relation to the underivatized form of the polysaccharide.

As an example, a maltodextrin having a starting weight of about 3000 Da is derivatized to provide pendent hexanoate groups that are coupled to the polysaccharide via ester linkages to provide a degree of substitution (DS) of about 2.5. This provides a hydrophobic polysaccharide having a theoretical molecular weight of about 8400 Da.

In forming the hydrophobic derivative of the natural biodegradable polysaccharide and as an example, a compound having a hydrocarbon segment can be covalently coupled to one or more portions of the polysaccharide. For example, the compound can be coupled to monomeric units along the length of the polysaccharide. This provides a polysaccharide derivative with one or more pendent groups. Each chemical group includes a hydrocarbon segment. The hydrocarbon segment can constitute all of the pendent chemical group, or the hydrocarbon segment can constitute a portion of the pendent chemical group. For example, a portion of the hydrophobic polysaccharide can have the following structural formula (1):

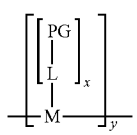

wherein each M is independently a monosaccharide unit, each L is independently a suitable linking group, or is a direct bond, each PG is independently a pendent group, each x is independently 0 to about 3, such that when x is 0, the bond between L and M is absent, and y is 3 or more.

Additionally, the polysaccharide that includes the unit of formula (1) above can be a

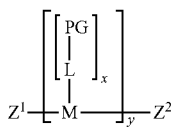

wherein each M is independently a monosaccharide unit, each L is independently a suitable linking group, or is a direct bond, each PG is independently a pendent group, each x is independently 0 to about 3, such that when x is 0, the bond between L and M is absent, y is about 3 to about 5,000, and $Z^1$ and $Z^2$ are each independently hydrogen, $OR^1$, $OC(=O)R^1$, $CH_2OR^1$, $SiR^1$ or $CH_2OC(=O)R^1$. Each $R^1$ is independently hydrogen, alkyl, cycloalkyl, cycloalkyl alkyl, aryl, aryl alkyl, heterocyclyl or heteroaryl, each alkyl, cycloalkyl, aryl, heterocycle and heteroaryl is optionally substituted, and each alkyl, cycloalkyl and heterocycle is optionally partially unsaturated.

For the compounds of formula (I) and (II), the monosaccharide unit (M) can include D-glucopyranose (e.g., α-D-glucopyranose). Additionally, the monosaccharide unit (M) can include non-macrocyclic poly-α(1→4) glucopyranose, non-macrocyclic poly-α(1→6) glucopyranose, or a mixture or combination of both non-macrocyclic poly-α(1→4) glucopyranose and non-macrocyclic poly-α(1→6) glucopyranose. For example, the monosaccharide unit (M) can include glucopyranose units, wherein at least about 90% are linked by α(1→4) glycosidic bonds. Alternatively, the monosaccharide unit (M) can include glucopyranose units, wherein at least about 90% are linked by α(1→6) glycosidic bonds. Additionally, each of the monosaccharides in the polysaccharide can be the same type (homopolysaccharide), or the monosaccharides in the polysaccharide can differ (heteropolysaccharide).

The polysaccharide can include up to about 5,000 monosaccharide units (i.e., y in the formula (1) or (II) is up to 5,000). Specifically, the monosaccharide units can be glucopyranose units (e.g., α-D-glucopyranose units). Additionally, y in the formula (1) or (II) can specifically be about 3-5,000 or about 3-4,000 or about 100 to 4,000.

In specific embodiments, the polysaccharide is non-macrocyclic. In other specific embodiments, the polysaccharide is linear. In other specific embodiments, the polysaccharide is branched. In yet further specific embodiments, the polysaccharide is a natural polysaccharide (PS).

The polysaccharide will have a suitable glass transition temperature (Tg). In one embodiment, the polysaccharide will have a glass transition temperature (Tg) of at least about 35° C. (e.g., about 40° C. to about 150° C.). In an embodiment, the polysaccharide will have a glass transition temperature (Tg) of −30° C. to about 0° C.

A "pendant group" refers to a group of covalently bonded carbon atoms having the formula $(CH_n)_m$, wherein m is 2 or greater, and n is independently 2 or 1. A hydrocarbon segment can include saturated hydrocarbon groups or unsaturated hydrocarbon groups, and examples thereof include alkyl, alkenyl, alkynyl, cyclic alkyl, cyclic alkenyl, aromatic hydrocarbon and aralkyl groups. Specifically, the pendant group includes linear, straight chain or branched $C_1$-$C_{20}$ alkyl group; an amine terminated hydrocarbon or a hydroxyl terminated hydrocarbon. In an embodiment, the pendant group includes polyesters such as polylactides, polyglycolides, poly (lactide-co-glycolide) co-polymers, polycaprolactone, terpolymers of poly (lactide-co-glycolide-co-caprolatone), or combinations thereof.

The monomeric units of the hydrophobic polysaccharides described herein typically include monomeric units having ring structures with one or more reactive groups. These reactive groups are exemplified by hydroxyl groups, such as the ones that are present on glucopyranose-based monomeric units, e.g., of amylose and maltodextrin. These hydroxyl groups can be reacted with a compound that includes a hydrocarbon segment and a group that is reactive with the hydroxyl group (a hydroxyl-reactive group).

Examples of hydroxyl reactive groups include acetal, carboxyl, anhydride, acid halide, and the like. These groups can be used to form a hydrolytically cleavable covalent bond between the hydrocarbon segment and the polysaccharide backbone. For example, the method can provide a pendent group having a hydrocarbon segment, the pendent group linked to the polysaccharide backbone with a cleavable ester bond. In these aspects, the synthesized hydrophobic derivative of the natural biodegradable polysaccharide can include chemical linkages that are both enzymatically cleavable (the polymer backbone) and non-enzymatically hydrolytically cleavable (the linkage between the pendent group and the polymer backbone).

Other cleavable chemical linkages (e.g., metabolically cleavable covalent bonds) that can be used to bond the pendent groups to the polysaccharide include carboxylic ester, carbonate, borate, silyl ether, peroxyester groups, disulfide groups, and hydrazone groups.

In some cases, the hydroxyl reactive groups include those such as isocyanate and epoxy. These groups can be used to form a non-cleavable covalent bond between the pendent group and the polysaccharide backbone. In these aspects, the synthesized hydrophobic derivative of the natural biodegradable polysaccharide includes chemical linkages that are enzymatically cleavable.

Other reactive groups, such as carboxyl groups, acetyl groups, or sulphate groups, are present on the ring structure of monomeric units of other natural biodegradable polysaccharides, such as chondrotin or hyaluronic acid. These groups can also be targeted for reaction with a compound having a hydrocarbon segment to be bonded to the polysaccharide backbone.

Various factors can be taken into consideration in the synthesis of the hydrophobic derivative of the natural biodegradable polysaccharide. These factors include the physical and chemical properties of the natural biodegradable polysaccharide, including its size, and the number and presence of reactive groups on the polysaccharide and solubility, the physical and chemical properties of the compound that includes the hydrocarbon segment, including its size and solubility, and the reactivity of the compound with the polysaccharide.

In preparing the hydrophobic derivative of the natural biodegradable polysaccharide any suitable synthesis procedure can be performed. Synthesis can be carried out to provide a desired number of groups with hydrocarbon segments pendent from the polysaccharide backbone. The number and/or density of the pendent groups can be controlled, for example, by controlling the relative concentration of the compound that includes the hydrocarbon segment to the available reactive groups (e.g., hydroxyl groups) on the polysaccharide.

The type and amount of groups having the hydrocarbon segment pendent from the polysaccharide is sufficient for the hydrophobic polysaccharide to be insoluble in water. In order to achieve this, as a general approach, a hydrophobic polysaccharide is obtained or prepared wherein the groups having the hydrocarbon segment pendent from the polysaccharide backbone in an amount in the range of 0.25 (pendent group): 1 (polysaccharide monomer) by weight.

The weight ratio of glucopyranose units to pendent groups can vary, but will typically be about 1:1 to about 100:1. Specifically, the weight ratio of glucopyranose units to pendent groups can be about 1:1 to about 75:1, or about 1:1 to about 50:1. Additionally, the nature and amount of the pendent group can provide a suitable degree of substitution to the polysaccharide. Typically, the degree of substitution will be in the range of about 0.1-5 or about 0.5-2.

To exemplify these levels of derivation, very low molecular weight (less than 10,000 Da) glucopyranose polymers are reacted with compounds having the hydrocarbon segment to provide low molecular weight hydrophobic glucopyranose polymers. In one mode of practice, the natural biodegradable polysaccharide maltodextrin in an amount of 10 g (MW 3000-5000 Da; ~3 mmols) is dissolved in a suitable solvent, such as tetrahydrofuran. Next, a solution having butyric anhydride in an amount of 18 g (0.11 mols) is added to the maltodextrin solution. The reaction is allowed to proceed, effectively forming pendent butyrate groups on the pyranose rings of the maltodextrin polymer. This level of derivation results in a degree of substitution (DS) of butyrate group of the hydroxyl groups on the maltodextrin of about 1.

For maltodextrin and other polysaccharides that include three hydroxyl groups per monomeric unit, on average, one of the three hydroxyl groups per glycopyranose monomeric unit becomes substituted with a butyrate group. A maltodextrin polymer having this level of substitution is referred to herein as maltodextrin-butyrate DS1. As described herein, the DS refers to the average number of reactive groups (including hydroxyl and other reactive groups) per monomeric unit that are substituted with pendent groups comprising hydrocarbon segments.

An increase in the DS can be achieved by incrementally increasing the amount of compound that provides the hydrocarbon segment to the polysaccharide. As another example, butyrylated maltodextrin having a DS of 2.5 is prepared by reacting 10 g of maltodextrin (MW 3000-5000 Da; ~3 mmols) with 0.32 mols butyric anhydride.

The degree of substitution can influence the hydrophobic character of the polysaccharide. In turn, implants formed from hydrophobic derivatives having a substantial amount of groups having the hydrocarbon segments bonded to the polysaccharide backbone (as exemplified by a high DS) are generally more hydrophobic and can be more resistant to degradation. For example, an implant formed from maltodextrin-butyrate DS1 has a rate of degradation that is faster than an implant formed from maltodextrin-butyrate DS2.

The type of hydrocarbon segment present in the groups pendent from the polysaccharide backbone can also influence the hydrophobic properties of the polymer. In one aspect, the implant is formed using a hydrophobic polysaccharide having pendent groups with hydrocarbon segments being short chain branched alkyl group. Exemplary short chain branched alkyl group are branched $C_4$-$C_{10}$ groups. The preparation of a hydrophobic polymer with these types of pendent groups is exemplified by the reaction of maltodextrin with valproic acid/anhydride with maltodextrin (MD-val). The reaction can be carried out to provide a relatively lower degree of substitution of the hydroxyl groups, such as is in the range of 0.5-1.5. Although these polysaccharides have a lower degree of substitution, the short chain branched alkyl group imparts considerable hydrophobic properties to the polysaccharide.

Even at these low degrees of substitution the MD-val forms coatings that are very compliant and durable. Because of the low degrees of substitution, the pendent groups with the branched $C_8$ segment can be hydrolyzed from the polysaccharide backbone at a relatively fast rate, thereby providing a biodegradable coatings that have a relatively fast rate of degradation.

For polysaccharides having hydrolytically cleavable pendent groups that include hydrocarbon segments, penetration by an aqueous solution can promote hydrolysis and loss of groups pendent from the polysaccharide backbone. This can alter the properties of the implant, and can result in greater access to enzymes that promote the degradation of the natural biodegradable polysaccharide.

Various synthetic schemes can be used for the preparation of a hydrophobic derivative of a natural biodegradable polysaccharide. In some modes of preparation, pendent polysaccharide hydroxyl groups are reacted with a compound that includes a hydrocarbon segment and a group that is reactive with the hydroxyl groups. This reaction can provide polysaccharide with pendent groups comprising hydrocarbon segments.

Any suitable chemical group can be coupled to the polysaccharide backbone and provide the polysaccharide with hydrophobic properties, wherein the polysaccharide becomes insoluble in water. Specifically, the pendent group can include one or more atoms selected from carbon (C), hydrogen (H), oxygen (O), nitrogen (N), and sulfur (S).

In some aspects, the pendent group includes a hydrocarbon segment that is a linear, branched, or cyclic $C_2$-$C_{18}$ group. More specifically the hydrocarbon segment includes a $C_2$-$C_{10}$, or a $C_4$-$C_8$, linear, branched, or cyclic group. The hydrocarbon segment can be saturated or unsaturated, and can include alkyl groups or aromatic groups, respectively. The hydrocarbon segment can be linked to the polysaccharide chain via a hydrolyzable bond or a non-hydrolyzable bond.

In some aspects the compound having a hydrocarbon segment that is reacted with the polysaccharide backbone is derived from a natural compound. Natural compounds with hydrocarbon segments include fatty acids, fats, oils, waxes, phospholipids, prostaglandins, thromboxanes, leukotrienes, terpenes, steroids, and lipid soluble vitamins.

Exemplary natural compounds with hydrocarbon segments include fatty acids and derivatives thereof, such as fatty acid anhydrides and fatty acid halides. Exemplary fatty acids and anhydrides include acetic, propionic, butyric, isobutyric, valeric, caproic, caprylic, capric, and lauric acids and anhydrides, respectively. The hydroxyl group of a polysaccharide can be reacted with a fatty acid or anhydride to bond the hydrocarbon segment of the compound to the polysaccharide via an ester group.

The hydroxyl group of a polysaccharide can also cause the ring opening of lactones to provide pendent open-chain hydroxy esters. Exemplary lactones that can be reacted with the polysaccharide include caprolactone and glycolides.

Generally, if compounds having large hydrocarbon segments are used for the synthesis of the hydrophobic derivative, a smaller amount of the compound may be needed for its synthesis. For example, as a general rule, if a compound having a hydrocarbon segments with an alkyl chain length of $C_x$ is used to prepare a hydrophobic derivative with a DS of 1, a compound having a hydrocarbon segment with an alkyl chain length of $C_{(x \times 2)}$ is reacted in an amount to provide a hydrophobic derivative with a DS of 0.5.

The hydrophobic derivative of the natural biodegradable polysaccharide can also be synthesized having combinations of pendent groups with two or more different hydrocarbon segments, respectively. For example, the hydrophobic derivative can be synthesized using compounds having hydrocarbon segments with different alkyl chain lengths. In one mode of practice, a polysaccharide is reacted with a mixture of two or more fatty acids (or derivatives thereof) selected from the group of acetic acid, propionic acid, butyric acid, isobutyric acid, valeric acid, caproic acid, caprylic acid, capric acid, and lauric acid to generate the hydrophobic derivative.

In other cases the hydrophobic derivative is synthesized having a non-hydrolyzable bond linking the hydrocarbon segment to the polysaccharide backbone. Exemplary non-hydrolyzable bonds include urethane bonds.

The hydrophobic derivative of the natural biodegradable polysaccharide can also be synthesized so that hydrocarbon segments are individually linked to the polysaccharide backbone via both hydrolyzable and non-hydrolyzable bonds. As another example, a hydrophobic derivative is prepared by reacting a mixture of butyric acid anhydride and butyl isocyanate with maltodextrin. This yields a hydrophobic derivative of maltodextrin with pendent butyric acid groups that are individually covalently bonded to the maltodextrin backbone with hydrolyzable ester linkages and non-hydrolyzable urethane linkages. The degradation of a coating having this type of hydrophobic derivative can occur by loss of the butyrate groups from hydrolysis of the ester linkages. However, a portion of the butyrate groups (the ones that are bonded via the urethane groups) are not removed from the polysaccharide backbone and therefore the natural biodegradable polysaccharide can maintain a desired degree of hydrophobicity, prior to enzymatic degradation of the polysaccharide backbone.

In some aspects, the group that is pendent from the polysaccharide backbone has properties of an active pharmaceutical ingredient (API). In this regard, the implants include polysaccharide-coupled API. In some aspects, an API which has a hydrocarbon segment can be hydrolyzed from the natural biodegradable polymer and released from the matrix to provide a therapeutic effect. One example of a therapeutically useful compound having a hydrocarbon segments is butyric acid, which has been shown to elicit tumor cell differentiation and apoptosis, and is thought to be useful for the treatment of cancer and other blood diseases.

Other illustrative compounds that include hydrocarbon segments include valproic acid and retinoic acid. These compounds can be coupled to a polysaccharide backbone to provide a pendent group, and then cleaved from the polysaccharide backbone upon degradation of the implant in vivo. Retinoic acid is known to possess antiproliferative effects and is thought to be useful for treatment of proliferative vitreoretinopathy (PVR). The pendent group that provides a therapeutic effect can also be a natural compound (such as butyric acid, valproic acid, and retinoic acid).

Another illustrative class of compounds that can be coupled to the polysaccharide backbone is the corticosteroids. An exemplary corticosteroid is triamcinolone. One method of coupling triamcinolone to a natural biodegradable polymer is by employing a modification of the method described in Cayanis, E. et al., Generation of an Auto-anti-idiotypic Antibody that Binds to Glucocorticoid Receptor, The Journal of Biol. Chem., 261(11): 5094-5103 (1986). Triamcinolone hexanoic acid is prepared by reaction of triamcinolone with ketohexanoic acid; an acid chloride of the resulting triamcinolone hexanoic acid can be formed and then reacted with the natural biodegradable polymer, such as maltodextrin or polyalditol, resulting in pendent triamcinolone groups coupled via ester bonds to the natural biodegradable polymer.

The hydrophobic derivative of the natural biodegradable polysaccharide can also be synthesized having two or more different pendent groups, wherein at least one of the pendent groups includes an API. The hydrophobic polysaccharide can be synthesized with an amount of a pendent groups including an API, that when released from polysaccharide, provides a therapeutic effect to the subject. An example of such a hydrophobic derivative is maltodextrin-caproate-triamcinolone. This hydrophobic derivative can be prepared by reacting a mixture including triamcinolone hexanoic acid and an excess of caproic anhydride (n-hexanoic anhydride) with maltodextrin to provide a derivative with a DS of 2.5.

In some aspects, the group that is pendent from the polysaccharide includes a hydrocarbon segment that is an aromatic group, such as a phenyl group. As one example, o-acetylsalicylic acid is reacted with a polysaccharide such as maltodextrin to provide pendent chemical group having a hydrocarbon segment that is a phenyl group, and a non-hydrocarbon segment that is an acetate group wherein the pendent group is linked to the polysaccharide via an ester bond.

Additional features and descriptions of the biodegradable polymers that include the hydrophobic derivatives of natural biodegradable polysaccharides (referred to as Eureka™ SOLO polymers) can be found, for example, in U.S. Patent Publication Nos. 2007/0218102, 2007/0260054 and 2007/0224247, and references cited therein.

Applying the Coating

As an example, a biodegradable coating on an expandable and collapsible structure can be made by preparing a coating composition including a biodegradable multiblock copolymer, such containing glycolic acid, caprolactone, and PEG polymeric blocks, dissolved in acetone at 30 mg/mL and applied by spraying the solution onto the structure (e.g., a balloon) (with or without a hydrogel base coat). Bioactive agent (e.g., in bioactive agent form) can be dissolved into the coating solution (1-50% by weight), or can be applied after the degradable coating is formed. For example, paclitaxel (dissolved in methanol, or present as bioactive agent in water) can be applied to the biodegradable coating.

The coating composition used to form the biodegradable coating can include one or more additional biocompatible polymers. For example, a secondary, tertiary, etc. biocompatible polymer can be included in the coating composition to form a coating with desired properties. The one or more additional polymers can increase the degradation of the coating. In some aspects, the biodegradable polymer is formed from a biodegradable polymer, such as polylactide, and a biocompatible polymer, such as one selected from the group consisting of poly(ethylene glycol) (PEG), poly(ethylene oxide), and polypropylene oxide).

Various methods can be performed to associate the polymeric material and the bioactive agent with the surface of the expandable and collapsible structure. In many modes of practice, a coating composition including polymeric material and bioactive agent is prepared and then applied to the surface of the expandable and collapsible structure. In one mode of practice a coating composition is used including bioactive agent at a concentration in the range of about 10 mg/mL to about 50 mg/mL.

However, in some cases polymeric material can be applied to the surface independently of the bioactive agent. For example, a polymeric composition can be applied to the surface in a first step, and then in a second step a composition having bioactive agent (and without polymeric coating material) can be to the applied to the previously coated polymer. In one mode of practice a coating composition having bioactive agent at a concentration in the range of about 10 mg/mL to about 50 mg/mL (without polymeric coating material) is used. Additional, optional, steps can be performed to apply the same or other polymeric material, such as a topcoat, over the bioactive agent.

In one preferred aspect, a coating is formed on the surface of the expandable and collapsible structure using a spray coating process. In a particular mode of practice a balloon catheter is mounted on an apparatus that can manipulate the balloon for coating using a spray deposition process.

Further aspects and details of the balloon coating apparatus and method can be found in commonly owned provisional Application having Ser. No. 61/188,929, filed on Aug. 14, 2008, and entitled METHOD AND APPARATUS FOR COATING BALLOON CATHETERS (Chappa et al.), the disclosure of which is incorporated herein by reference.

Alternatively, a coating composition is dip-coated onto the surface of the expandable and collapsible structure to form a coated surface. In yet another method, the composition is brushed onto the surface of the expandable and collapsible structure. In some applications, the substrate can be subject to more than one step of coating with a mixture of polymeric material and bioactive agent, thereby allowing the formation of multiple layers on the substrate surface.

In some aspects, a coating is prepared by treating the coating materials that are disposed on the expandable and collapsible structure. For example, the coating composition can include a reactive group, that when activated, causes crosslinking of polymeric material and formation of the coating. The polymeric material used to form the coating can include pendent polymerizable groups, such as acrylate groups. The free radical polymerization of the polymerizable groups can be caused by the activation of a photoactivatable reagent that is a polymerization initiator. The applied composition can be treated with UV light to activate the polymerization initiator.

Particles of bioactive agent can be associated with the coating to provide partially embedded particles using a variety of techniques. In one technique a flexible hydrogel layer is formed on the surface of the expandable and collapsible structure. Next an aqueous composition containing bioactive agent is disposed on the surface of the flexible hydrogel layer. The water in the aqueous composition causes at least the surface of the flexible hydrogel layer to swell. The swelling makes the flexible hydrogel layer at least partially permeable to the bioactive agent deposited on the hydrogel layer, and bioactive agent move into the polymeric material of hydrogel layer. After a sufficient amount of time allowing for the bioactive agent to move partially into the hydrogel layer, water can then be removed, such as by evaporation, heating, or vacuum. Removal of water causes the hydrogel layer to shrink from a swollen state, physically constrain the bioactive agent, and results in the partial embedding of a substantial portion of the bioactive agent deposited on the surface of the hydrogel layer.

Medical Devices

The present invention provides methods and devices for the delivery of a bioactive agent to a target tissue. The present invention contemplates various types of medical devices that include an expandable and collapsible structure from which a bioactive agent can be released. In one embodiment, the insertable medical device is a balloon catheter. The bioactive agent is associated with an expandable and collapsible surface of an insertable medical device via a coated material. The device can be inserted into a subject to place the expandable and collapsible surface in contact with a target tissue to which the bioactive agent can be transferred. The expandable and collapsible surface can be expanded, causing release or dissociation of the bioactive agent (e.g., in microparticulate form) from coating on the surface of the expandable and collapsible structure. Alternatively, the expandable and collapsible surface can include a biodegradable coated material that is released from the expandable collapsible structure when it is expanded, resulting in the transfer of the biodegradable coated material along with the bioactive agent (e.g., microparticulate).

The expandable and collapsible structure of the device can be formed from any material, or combination of materials, capable of expanding, and suitable for use within the body. The one or more material(s) can be based on use of the device. In many aspects the expandable and collapsible materials are compliant and flexible materials, such as elastomers (polymers with elastic properties). Elastomers are typically thermoplastic polymers. Exemplary elastomers can be formed from various polymers including polyurethanes and polyurethane copolymers, polyethylene, styrene-butadiene copolymers, polyisoprene, isobutylene-isoprene copolymers (butyl rubber), including halogenated butyl rubber, butadiene-styrene-acrylonitrile copolymers, silicone polymers, fluorosilicone polymers, polycarbonates, polyamides, polyesters, polyvinyl chloride, polyether-polyester copolymers, and polyether-polyamide copolymers.

The expandable and collapsible structure can be made of a single elastomeric material, or a combination of materials. The expandable and collapsible structure can be manufactured by an extrusion process, so that the elastic structure is a single layer of material, or co-extruded to form a multi-layered material.

The elastic structure can have a thickness suitable for the desired application and device. For example, the thickness of an elastic structure can be in the range of about 5 μm to about 100 μm.

The manufacture of expandable and collapsible structures is well known in the art, and any suitable process can be carried out to provide the expandable substrate portion of the insertable medical device as described herein.

Balloon Catheters

In an embodiment, the insertable medical device has an expandable and collapsible structure that includes or is a balloon, e.g., an angioplasty balloon. Such a device can be used for the treatment of diseased vasculature. Suitable bioactive agents that can be released to the vasculature include an antiproliferative agent, an antiinflamatory agent, an antiplatelet agent, or plurality thereof. Suitable antiproliferative agents include paclitaxel. Balloon catheters are commonly used in angioplasty procedures for the treatment of arteries that are diseased. Balloon angioplasty generally involves the dilation or reopening of blocked intraluminal channels.

Balloon catheter constructions are well known in the art and are described in various documents, for example, U.S. Pat. Nos. 4,195,637, 5,041,089, 5,087,246, 5,318,587, 5,382,234, 5,571,089, 5,776,101, 5,807,331, 5,882,336, 6,394,995, 6,517,515, 6,623,504, 6,896,842, and 7,163,523. Balloon catheters generally include four portions, the balloon, catheter shaft, guidewire, and manifold. A balloon catheter generally includes an elongated catheter shaft with the inflatable balloon attached to a distal section of the catheter shaft. At a proximal end of the catheter shaft, there is typically a manifold. At the manifold end, placement of the catheter can be facilitated using a guidewire. Guidewires are small and maneuverable when inserted into an artery. Once the guidewire is moved to the target location, the catheter with balloon portion is then fed over the guidewire until the balloon reaches the target location in the vessel. The balloon is then inflated when the catheter reaches the targeted constriction to thereby apply the requisite mechanical force to cause vessel dilation. The manifold can also control the fluid introduction within shaft for expansion of the balloon. The balloon is typically inserted into the arterial lumen of a patient and advanced through the lumen in an unexpanded state.

Prior to inflation the balloon can be folded to a compacted configuration for delivery to the target site. A folding process may involve creating "arms" of the balloon material and folding these arms inward (towards the catheter axis) to compact the balloon material. Using such a folding pattern, there will be portions of the balloon material (when the balloon is folded and compacted) that face the outside, and portions of the balloon material that face the inside, the inner-facing portions representing "protected" surfaces. Accordingly, and in another coating embodiment, the inner-facing surfaces of the balloon material include the present coating.

The balloon is typically inflated using a fluid, which is injected through an inflation port. The mechanics of fluid transfer and introduction within balloons vary according to the specific design of the catheter, and are well know in the art.

Exemplary thicknesses for the walls of catheter balloons are in the range of about 5 μm to about 20 μm. The actual thickness of the balloon wall may depend on one or more factors, such as the desired pliability of the balloon, the overall profile of the balloon on the catheter (low profile devices may use thin walled balloons), the pressure rating for the balloon wall, or the expansion properties of the balloon. In some cases, a balloon with a thin wall is used, so as to accommodate the increase in thickness when a coating is formed on the surface.

Catheter balloon construction is described in various references, for example, U.S. Pat. Nos. 4,490,421, 5,556,383, 6,210,364, 6,168,748, 6,328,710, and 6,482,348. Molding processes are typically performed for balloon construction. Balloons fabricated by such processes are suitable as substrates for the coatings according to the present invention. In an exemplary molding process, an extruded polymeric tube is radially and axially expanded at elevated temperatures within a mold having the desired shape of the balloon. The balloon can be subjected to additional treatments following the molding process. For example, the formed balloon can be subjected to additional heating steps to reduce shrinkage of the balloon.

Transfers of bioactive agent from a paclitaxel microparticulate-coated balloon having a hydrogel coating and lipid coating can be tested in a silicone tube model. Silicone tubing (inner diameter: 0.125 inch; outer diameter: 0.188 inch; wall: 0.0315 inch; Cole-Parmer Instrument Co.) is obtained and cut into 1.5 inch lengths. The silicone tubing pieces are then placed individually in a 4 mL amber glass vial filled with 4 mL of PBS (phosphate buffer saline) pH-7.4, which is preheated in a water bath to 37° C. A coated (see, e.g., the Examples), deflated, folded balloon is placed in an 8 mL vial (holding 8 mL of phosphate buffer saline at pH 7.4, which is preheated in a water bath to 37° C.) for soaking for 4 min. The balloon is then slid into the inner lumen of the silicone tube (submerged inside 4 mL vial) and then expanded for 30 sec at 4 atm. Pressure is then released and the balloon is removed from the tubing. To determine the amount of paclitaxel transferred to the wall of the inner lumen of the tubing, the tubing is submerged in 4 mL of a mixture of 0.1% glacial acetic acid in methanol for 24 hours. A 350 μL aliquot of the extraction media is then transferred to 96 well plate for drug content measurement by UV (@ 232 nm).

A coating composition for forming a hydrogel coated layer on a catheter balloon can be as follows. A hydrogel coating solution is prepared using photo-polyacrylamide at 5 mg/mL, photo-poly(vinylpyrrolidone) (as described in Example 4 of U.S. Pat. No. 5,414,075) at 25 mg/mL, poly(vinylpyrrolidone) K90 (BASF) at 10 mg/mL, and 4,5-bis(4-benzoylphenylmethyleneoxy)benzene-1,3-disulfonic acid (as described in U.S. Pat. No. 6,278,018 (Example 1)) at 0.25 mg/mL, is dissolved into a mixture of IPA and water (15% IPA/85% water).

Bioactive Agent

The term "bioactive agent," refers to an inorganic or organic molecule, which can be synthetic or natural, that causes a biological effect when administered in vivo to an animal, including but not limited to birds and mammals, including humans. A partial list of bioactive agents is provided below. One may choose any one of the bioactive agents to be included alone, or in combination with any other bioactive agent. A comprehensive listing of bioactive agents, in addition to information of the water solubility of the bioactive agents, can be found in *The Merck Index*, Thirteenth Edition, Merck & Co. (2001).

The bioactive agent(s) can be, for example, one or more of the following classes of agents: ACE inhibitors, actin inhibitors, analgesics, anesthetics, anti-hypertensives, anti polymerases, antisecretory agents, antibiotics, anti-cancer substances, anti-cholinergics, anti-coagulants, anti-convulsants, anti-depressants, anti-emetics, antifungals, anti-glaucoma solutes, antihistamines, antihypertensive agents, anti-inflammatory agents (such as NSAIDs), anti metabolites, antimitotics, antioxidizing agents, anti-parasite and/or anti-Parkinson substances, antiproliferatives (including antiangiogenesis agents), anti-protozoal solutes, anti-psychotic substances, anti-pyretics, antiseptics, anti-spasmodics, antiviral agents, calcium channel blockers, cell response modifiers, chelators, chemotherapeutic agents, dopamine agonists, extracellular matrix components, fibrinolytic agents, free radical scavengers, growth hormone antagonists, hypnotics, immunosuppressive agents, immunotoxins, inhibitors of surface glycoprotein receptors, microtubule inhibitors, miotics, muscle contractants, muscle relaxants, neurotoxins, neurotransmitters, polynucleotides and derivatives thereof, opioids, prostaglandins, remodeling inhibitors, statins, steroids, thrombolytic agents, tranquilizers, vasodilators, and vasospasm inhibitors.

In some aspects the microparticulate include an antiproliferative agent. The antiproliferative agent can be an anti-angiogenesis agent.

In some aspects the microparticulate include an anti-inflammatory agent.

In some aspects the microparticulate include a cell response modifier.

In some aspects the microparticulate include an antithrombotic agent.

In some aspects the microparticulate include an immunosuppressive agent.

Cell response modifiers include chemotactic factors, such as platelet-derived growth factor (pDGF). Other chemotactic factors include neutrophil-activating protein, monocyte chemoattractant protein, macrophage-inflammatory protein, SIS (small inducible secreted) proteins, platelet factor, platelet basic protein, melanoma growth stimulating activity, epidermal growth factor, transforming growth factor (alpha), fibroblast growth factor, platelet-derived endothelial cell growth factor, insulin-like growth factor, nerve growth factor, vascular endothelial growth factor, bone morphogenic proteins, and bone growth/cartilage-inducing factor (alpha and beta).

Other cell response modifiers are the interleukins, interleukin inhibitors or interleukin receptors, including interleukin 1 through interleukin 10; interferons, including alpha, beta and gamma; hematopoietic factors, including erythropoietin, granulocyte colony stimulating factor, macrophage colony stimulating factor and granulocyte-macrophage colony stimulating factor; tumor necrosis factors, including alpha and beta; transforming growth factors (beta), including beta-1, beta-2, beta-3, inhibin, activin, and DNA that encodes for the production of any of these proteins.

Examples of statins include lovastatin, pravastatin, simvastatin, fluvastatin, atorvastatin, cerivastatin, rosuvastatin, and superstatin.

Examples of steroids include glucocorticoids such as cortisone, hydrocortisone, dexamethasone, betamethasone, prednisone, prednisolone, methylprednisolone, triamcinolone, beclomethasone, fludrocortisone, and aldosterone; sex steroids such as testosterone, dihydrotestosterone, estradiol, diethylstilbestrol, progesterone, and progestins.

The bioactive agent can provide antirestenotic effects, such as antiproliferative, anti-platelet, and/or antithrombotic effects. In some embodiments, the bioactive agent can be selected from anti-inflammatory agents, immunosuppressive agents, cell attachment factors, receptors, ligands, growth factors, antibiotics, enzymes, nucleic acids, and the like. Compounds having antiproliferative effects include, for example, actinomycin D, angiopeptin, c-myc antisense, paclitaxel, taxane, and the like.

Representative examples of bioactive agents having antithrombotic effects include heparin, heparin derivatives, sodium heparin, low molecular weight heparin, hirudin, lysine, prostaglandins, argatroban, forskolin, vapiprost, prostacyclin and prostacyclin analogs, D-phe-pro-arg-chloromethylketone (synthetic antithrombin), dipyridamole, glycoprotein Iib/IIIa platelet membrane receptor antibody, coprotein Iib/IIIa platelet membrane receptor antibody, recombinant hirudin, thrombin inhibitor (such as commercially available from Biogen), chondroitin sulfate, modified dextran, albumin, streptokinase, tissue plasminogen activator (TPA), urokinase, nitric oxide inhibitors, and the like.

The bioactive agent can also be an inhibitor of the GPIIb-IIIa platelet receptor complex, which mediates platelet aggregation. GPIIb/IIIa inhibitors can include monoclonal antibody Fab fragment c7E3, also know as abciximab (ReoPro™), and synthetic peptides or peptidomimetics such as eptifabatide (Integrilin™) or tirofiban (Agrastat™).

The bioactive agent can be an immunosuppressive agent, for example, cyclosporine, CD-34 antibody, everolimus, mycophenolic acid, sirolimus, tacrolimus, and the like.

Additionally, the bioactive agent can be a surface adhesion molecule or cell-cell adhesion molecule. Exemplary cell adhesion molecules or attachment proteins, such as extracellular matrix proteins, include fibronectin, laminin, collagen, elastin, vitronectin, tenascin, fibrinogen, thrombospondin, osteopontin, von Willibrand Factor, bone sialoprotein (and active domains thereof), and hydrophilic polymers such as hyaluronic acid, chitosan and methyl cellulose, and other proteins, carbohydrates, and fatty acids. Other cell-cell adhesion molecules include N-cadherin and P-cadherin and active domains thereof.

An antiproliferative agent, such as sirolimus or paclitaxel, can inhibit neointimal proliferation at a dilated site. An antithrombotic agent, such as heparin, can inhibit clotting.

The present device and method can release an effective amount of the bioactive agent at the desired site. In certain embodiments, the method and device can release about 10% or more of the bioactive agent originally associated with the device, about 20% or more, about 30% or more, about 40% or more, about 50% or more, about 60% or more, about 70% or more, about 80% or more, or about 90% or more. In some aspects the amount of bioactive agent transferred is in the range of about 30% to about 90%.

Additional Ingredients

The bioactive agent can be formulated with an excipient. Excipients can improve the stability of the bioactive agent within the coating, or can change physical properties of the bioactive agent. Exemplary excipients include glycerol, diethylene glycol, sorbitol, sorbitol esters, maltitol, sucrose, fructose, invert sugars, corn syrup, and mixtures thereof. The amount and type of excipient(s) can be based on known standards and techniques. The excipient can be an antioxidant.

The coating can include an imaging component. An imaging component can be detectable using common imaging techniques and suitable for use in the inventive methods. These agents can be capable of allowing imaging of a desired site in the body, e.g., an intravascular target site. Examples of imaging agents include substances having a label that is detectable in vivo, e.g., antibodies attached to fluorescent labels, paramagnetic materials, such as iron oxide, Gd, or Mn, or a radioisotope. Imaging components can be detected by paramagnetic resonance imaging, ultrasonic imaging, or other suitable detection techniques.

Microparticulate

The bioactive agent can be in the form of a microparticulate. The microparticulate can be any three-dimensional particle of size and shape sufficient to be associated with the substrate via coating materials, and then dissociated upon its expansion of the substrate.

The microparticulate can have a spherical, or substantially spherical shape, such as those that are formed from synthetic polymeric materials. In many aspects, the elastic structure of the device is associated with spherical or substantially spherical microparticulate, which is herein referred to as a "microsphere."

However, microparticulate can be used that have noticeably non-spherical shapes or irregular shapes (for example, when examined by microscopy). For example, the microparticulate can have curved surfaces, flat surfaces, or combinations thereof. If desired, the expandable and collapsible structure can be associated with a plurality of microparticulate of a combination of different sizes and/or shapes.

Microparticulate can be in the form of microcrystals or particles that otherwise have crystalline shapes or configurations. Microparticulate with crystalline shapes may be composed of bioactive agent molecules that are arranged in the microparticulate in an orderly repeating pattern extending in all three spatial dimensions. Crystalline shapes can typically be observed under the microscope. Microcrystals may be observed as having rod-like, filament-like, sliver-like, or needle-like shapes.

In association with the coating on the substrates, microparticulate may also be observed (or exist in) as aggregated or clumped structures. For example, aggregates of microparticulate having rod-like, filament-like, sliver-like, or needle-like shapes can be associated with the coating materials.

In many aspects, microparticulate associated with the expandable and collapsible structure have a greatest average dimension that is less than about 50 µm. For example, for microparticulate can have an elongated shape, with a length along the elongate axis of less than about 50 µm. Size analysis, such as by microscopy, can be used to assess irregular shaped microparticulate or microcrystal. In some cases, the microparticulate have a greatest average dimension in the range of about 100 nm to about 50 µm, about 100 nm to about 25 µm, about 100 nm to about 20 µm, or about 100 µm to about 10 µm.

Also, in many aspects, the microparticulate have a spherical or substantially spherical shape with an average diameter of about 100 nm or larger. For example, the microparticulate associated with the expandable and collapsible structure can have an average diameter in the range of about 100 nm to about 50 µm, about 150 nm to about 25 µm, about 200 nm to about 20 µm, or about 0.3 µM to about 10 µm.

In many aspects, microparticulate associated with the expandable and collapsible structure have an average diameter ("dn", number average) that is less than about 50 µm. Also, in many aspects, the microparticulate can have an average diameter of about 100 nm or larger. For example, the microparticulate associated with the expandable and collapsible structure can have an average diameter in the range of about 100 nm to about 50 µM, about 150 nm to about 25 µm, about 200 nm to about 20 µm, or about 0.3 µm to about 10 µm.

Depending on the manner by which the microparticulate is associated with the expandable and collapsible structure, it can be desirable to use microparticulate within a particular size range. For example, when the microparticulate is immobilized in a coating on the surface of the elastic structure, it is generally desirable to utilize microparticulate having an average diameter that is smaller than the thickness of the coating.

In some aspects, the microparticulate associated with the elastic surface can also have a low size polydispersity. Low size dispersity means that there is little variation in the size of the microparticulate in the population of microparticulate (as compared to a high size dispersity, which means that there is considerable variation in the size of the microparticulate population).

In some embodiments, the microparticulate can be formed completely or substantially of a selected bioactive agent for treatment or prevention of a condition. In other embodiments, the microparticulate can be formed from a combination of bioactive agents (e.g., two or more different bioactive agents). In other embodiments, the microparticulate can be formed from a bioactive agent and another component that is not intended to provide a therapeutic effect to the subject, such as a polymer that can modulate the release of the bioactive agent from the microparticulate. In other embodiments the microparticulate include two or more components, such as two or more polymers that modulate the release of the bioactive agent from the microparticulate.

Components of the microparticulate can be in mixture with one another in a portion of, or all of, the microparticulate. Alternatively, the components can be entirely or substantially separated from one another in the microparticulate. For example, the microparticulate can be formed including a substantially homogenous mixture of a bioactive agent and a release-modulating polymer. As another example, the microparticulate can be formed including a bioactive agent core and a release-modulating polymer shell around the core. The preparation of paclitaxel microparticles has been described in U.S. Pat. No. 6,610,317.

Other techniques for the preparation of microparticulate is known in the art and include precipitation and crystallization. For example, a liquid composition of a bioactive agent in a solvent (e.g., an organic solvent) can be precipitated by addition of an excess of a non-solvent (e.g., water or an aqueous composition). The solvent can be removed from the liquid composition by phase separation, or a comparable technique. The precipitated composition can then be subjected to comminution, which refers to mechanical process that can reduce the size of the precipitated particulates. For example, wet milling can be used to reduce particle size in a liquid composition and produce microparticulate. The precipitated bioactive agent can then be filtered and washed with the non-solvent.

Another process that can be used for the preparation of microparticulate is spray drying. A liquid composition of the bioactive agent and solvent can be atomized and spray deposited on a substrate, and during the process the solvent is evaporated from the droplets. The concentration of the bioactive agent, the droplet size, and the evaporation of the solvent can be determined to provide desired microparticulate formation.

In some modes of preparing the coating, a spray drying process is performed by directly spraying a liquid composition of the bioactive agent onto a coated layer (for example, the flexible hydrogel layer or a biodegradable material layer) of the device. In this process, the microparticulate is formed on the coated layer as the solvent from the droplets evaporates. The sprayed composition may also include a liquid that causes the swelling of the hydrogel layer. Therefore, as the microparticulate form they also move into the hydrogel material. As the non-solvent evaporates, the hydrogel shrinks and the microparticulate become constrained by the hydrogel material and at least partially embedded in the flexible hydrogel coating.

As another example, therapeutic Fab (antibody) fragment microspheres, are described in commonly-assigned copending U.S. provisional patent application No. 60/937,492, filed Jun. 28, 2007 to Slager, et al. Therefore, in another aspect of the invention, the microparticulate is composed of higher molecular weight bioactive agents, such as polypeptides.

Degradable microparticulate can be prepared incorporating various biologically active agents by established techniques, for example, the solvent evaporation technique (see, for example, Wiehert, B. and Rohdewald, P. J Microencapsul. (1993) 10:195).

In some aspects, the microparticulate includes a bioactive agent and a polymer, wherein the microparticulate has a structure that includes an inner portion including the bioactive agent and an outer portion including polymer. For example, the microparticulate can have a bioactive agent core and polymer shell.

In some aspects, the core of the microparticulate is formed substantially or entirely of bioactive agent, and the shell includes a biodegradable polymer.

In some aspects, the core of the microparticulate is includes a bioactive agent and a first polymer, and the shell includes a second polymer, such as a biodegradable polymer. For example, the first and second polymers are selected from synthetic biodegradable polymers.

The inner portion (e.g., core) of the microparticulate includes at least most of, if not all, of the bioactive agent present in the microparticulate. Various techniques can be used to prepare microparticulate having inner and outer portions (see, for example, Pekarek, K. J. (1994) Nature 367: 258-60). Some techniques are based on phase separation of a polymer mixture. Many phase separation techniques also involve solvent evaporation.

Microparticulate including an inner portion and an outer portion can be prepared by first preparing a first composition that includes the first polymer and the bioactive agent. The first composition can be treated to provide a homogenous suspension of the first polymer and the bioactive agent. The homogenized first composition can then be combined with a second composition that includes the second polymer. The mixture of the first and second compositions can then be homogenized. After these steps microparticulate can be formed by combining the composition with a solution that promotes formation of the microparticulate, such as a polyvinylalcohol-containing solution. In one mode of practice, the microparticulate can then be recovered by, for example, centrifugation, and then optionally washed, and frozen or lyophilized.

In some specific aspects, the inner portion of the microparticulate include a synthetic biodegradable copolymer, such as poly(lactide-co-glycolide) and an outer portion of the microparticulate include a synthetic biodegradable homopolymer, such as poly(lactide).

The microparticulate can also include one or more non-polymeric compounds to control release of the bioactive agent. For example, the microparticulate can include a soluble metal or metal salt to control release of the bioactive agent. Exemplary metal salts inorganic metal chlorides, fluorides, and oxides. The metal salt can be slightly soluble in water. The microparticulate can be partially or wholly coated with a metal salt.

In some aspects the elastic surface is associated with two or more sets of microparticulate. The use of two or more sets of microparticulate may allow a particular bioactive agent to be released at different rates after the microparticulate have been transferred to tissue, or may allow two different types of bioactive agents to be released to a subject. For example, a first bioactive agent can be released from a first set of microparticulate and a second bioactive agent can be released from a second set of microparticulate.

Two sets of microparticulate can be used if it is desired to deliver two bioactive agents which are mutually incompatible in a particular environment, for example, as hydrophobic and hydrophilic drugs are incompatible in either a polar or non-polar solvent. For example, the first bioactive agent can be a hydrophobic drug present in a first set of microparticulate, and the second bioactive agent can be a hydrophilic drug present in a second set of microparticulate. Useful degradable polymers or degradable copolymers for hydrophobic drugs have a high lactide or high caprolactone content; whereas useful degradable polymers or degradable copolymers for hydrophilic drugs have high glycolide content.

The present invention may be better understood with reference to the following examples. These examples are intended to be representative of specific embodiments of the invention, and are not intended as limiting the scope of the invention.

EXAMPLES

Example 1

The Present Barrier Layer Increases Drug Delivery to Tissue

An embodiment of the present barrier layer, a coating composition of 50 wt-% dodecanoic acid and 50 wt-% oleic acid, increased transfer of paclitaxel from a balloon catheter to arterial tissue in an ex-vivo model.

Materials and Methods

Coating the Catheter

The expandable and collapsible surface of the balloon of a balloon catheter was provided with a flexible hydrogel coating with associated paclitaxel microparticulate. The balloon catheter was obtained from Minnesota Medtec (Maple Grove, Minn.). The expandable and collapsible structure of the balloon was made from nylon with a balloon wall thickness of 5-10 μM.

A hydrogel coating solution was prepared using photo-polyacrylamide (as described in U.S. Pat. No. 6,007,833, which was weighed and dissolved into a mixture of IPA and water (50% IPA/50% water (v/v)) at a concentration of 10 mg/mL. The balloon was coated in the photo-polyacrylamide coating solution using a dip process with a withdrawal rate of 0.5 cm/s. After the hydrogel coating solution was applied to the balloon, it was subjected to UV cure. The coated balloon was placed in front of a Dymax 2000-EC Series UV Floodlamb with a 400 Watt metal halide bulb, approximately 20 cm from light source, illuminated for three minutes, and then removed.

Next, paclitaxel microparticulate was prepared using a wet milling process. Briefly, neat drug was added directly to DI water at 20 mg/mL. The precipitated paclitaxel particulates were then milled in water to reduce the particle size to ~1-3 μm. The drug/water suspension was tumble milled in a glass jar with ceramic beads. The suspension was milled for 16 hours (overnight) at approximately 100 rpm. The resulting suspension was then applied to the photo-polymer coated surface by pipetting a known volume of drug suspension (typically 20 μl). The pipetted droplet was evenly distributed over the balloon surface by rotating the balloon until the solvent was visibly dry. Then, the balloon was pleated and folded.

The present lipid coating was then applied by dipping the folded, coated, paclitaxel bearing catheter balloon into the melted lipid coating composition at 40° C. at 0.5 to 1 cm/sec. After dipping the coated balloon was kept at room temperature for 1 to 4 hours. Then the coated balloon was cooled at −20° C. and a protective sheath was put over the coating.

Ex Vivo Testing

Harvested porcine artery was obtained and cut into 1.5 inch lengths. The porcine artery pieces were then placed in a 4 mL amber glass vial filled with 4 mL of PBS (phosphate buffered saline) at pH 7.4, which was preheated in a water bath to 37° C.

A deflated, folded balloon was placed in an 8 mL vial that had been filled with 8 mL of PBS at pH 7.4 and preheated in a water bath to 37° C. and soaked for 4 min. The balloon was put through a 7 French guide catheter. After it exited the guide catheter it was inserted into the artery. The balloon was slid into the inner lumen of the porcine artery (submerged inside 4 mL vial) and then expanded for 30 sec at 4 atm. Pressure was then released and the balloon was removed from the porcine artery.

To determine the amount of paclitaxel transferred to the wall of the inner lumen of the porcine artery, the porcine artery was submerged in 4 mL of a mixture of 0.1% glacial acetic acid in methanol for 24 hours. A 1 mL aliquot of the extraction media was then transferred to 96 well plate for drug content measurement by UV. The amounts of paclitaxel transferred to the porcine artery were measured and reported.

Results and Conclusion

Figure 2:
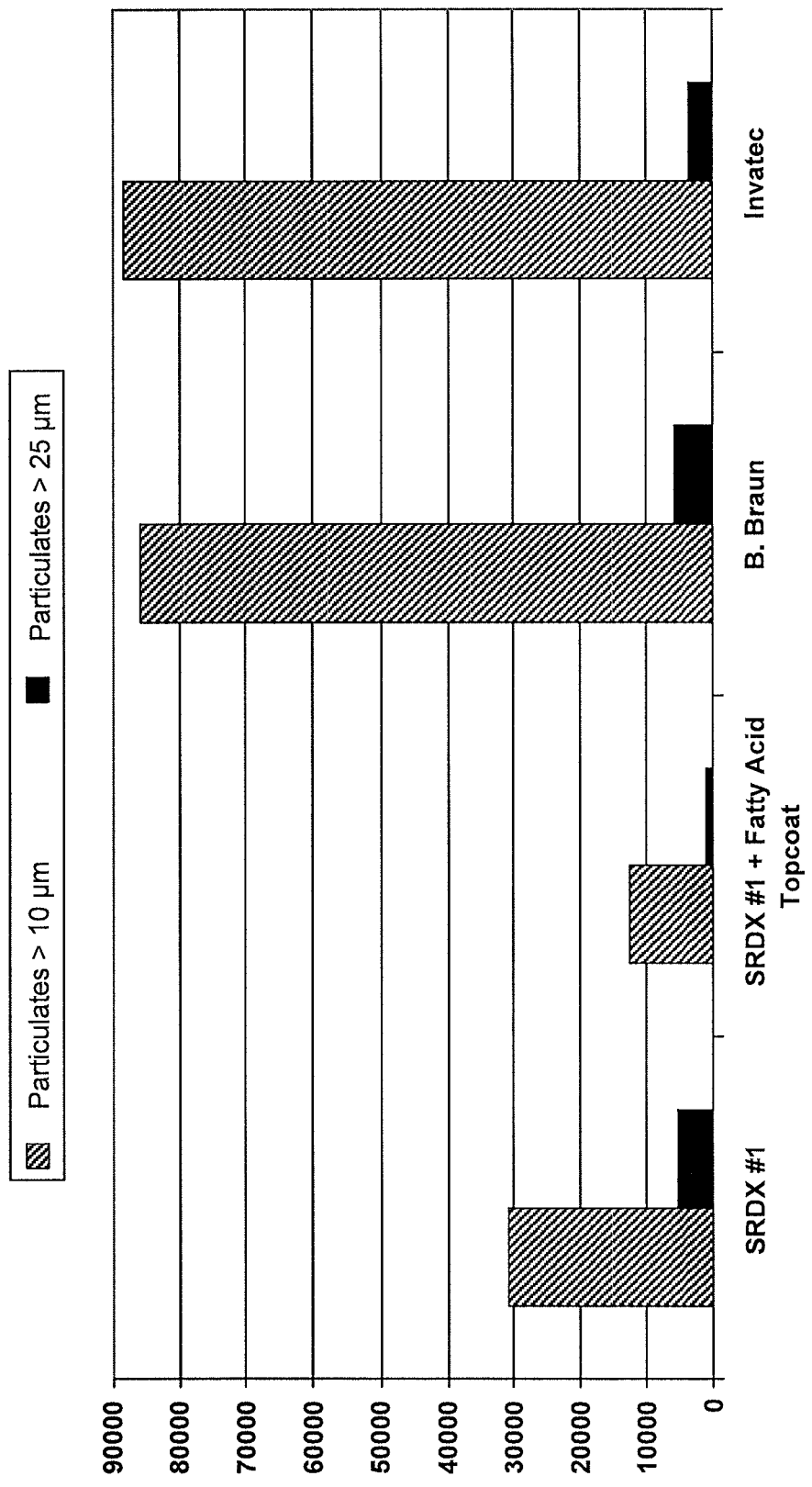
FIG. 2 illustrates that the present lipid coating significantly decreased release of particles from a coated catheter balloon in simulated use testing.

The present lipid coating significantly decreased release of particles from a coated catheter balloon in simulated use testing (FIG. 2). The catheter was put through a tortuous path, inflated, deflated, and retracted. Data set 1 shows release of particles in the absence of the present lipid coating when the particles are embedded in a hydrogel coating. Data set two, illustrates significantly reduced release of particles when the hydrogel coating including drug particles has been covered by an embodiment of the present lipid coating composition (50 wt-% dodecanoic acid and 50 wt-% oleic acid). Data sets three and four illustrates particle release from a first and second catheter system in the absence of either the hydrogel or the lipid coating. The results were normalized for a 3.5×15 mm balloon size.

Figure 3:
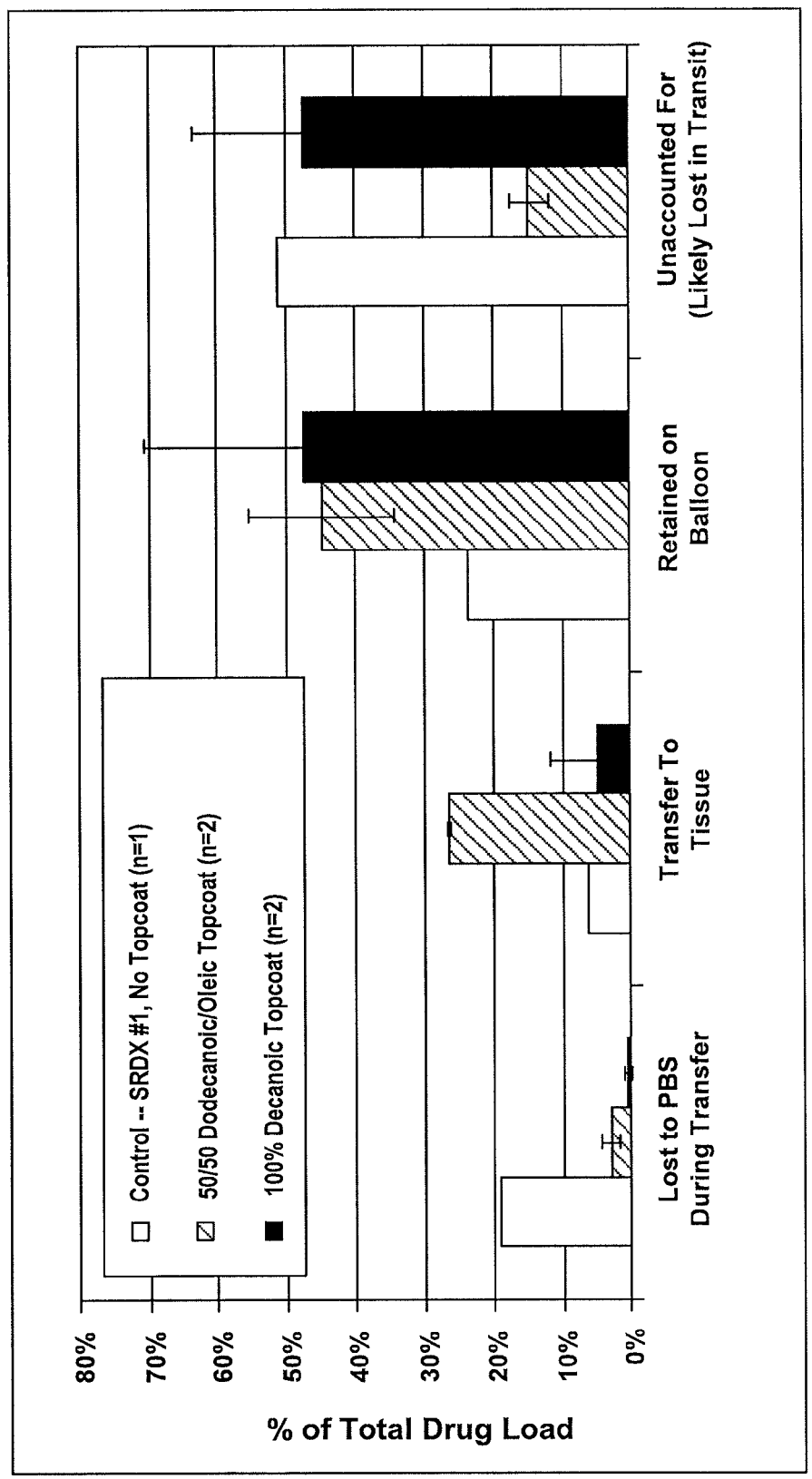
FIG. 3 illustrates that the present lipid coating increased transfer of drug to tissue as well as decreasing loss of drug in ex vivo testing.

FIG. 3 illustrates that the present lipid coating increased transfer of drug to tissue as well as decreasing loss of drug in ex vivo testing. The middle bar in each set shows the amount of drug found in a location when using a catheter coated with an embodiment of the present lipid coating composition (50 wt-% dodecanoic acid and 50 wt-% oleic acid). The left bar in each set represents location of drug when the catheter included the hydrogel coating but no fatty acid coating. The right bar in each set represents the location of drug when the fatty acid coating composition was 100 wt-% dodecanoic acid. The data illustrates that more drug is delivered to the tissue and less is lost in transfer or unaccounted for with use of the present lipid coating composition.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

It should also be noted that, as used in this specification and the appended claims, the term "configured" describes a system, apparatus, or other structure that is constructed or configured to perform a particular task or adopt a particular configuration. The term "configured" can be used interchangeably with other similar phrases such as arranged and configured, constructed and arranged, adapted and configured, adapted, constructed, manufactured and arranged, and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

The invention has been described with reference to various specific and preferred embodiments and techniques. However, it should be understood that many variations and modifications may be made while remaining within the spirit and scope of the invention.

We claim:

1. A medical device comprising:
   a balloon,
   a coating on all or a portion of the balloon, the coating comprising (i) nano- or microparticles that comprise a bioactive agent and (ii) a flexible hydrogel matrix, and
   a lipid coating on the coating comprising the bioactive agent, the lipid coating having a melting or softening point greater than room temperature and less than body temperature of the subject and comprising a plurality of fatty acids;
   the device being effective for delivering the bioactive agent to a site within a subject.

2. The device of claim 1, wherein the lipid coating comprises two fatty acids.

3. The device of claim 1, wherein the plurality of fatty acids is a mixture of fatty acids that are solid at room temperature and soft or liquid at body temperature of the subject.

4. The device of claim 1, wherein the plurality of fatty acids is a mixture of fatty acids that comprises oleic acid, dodecanoic acid, or salt thereof.

5. The device of claim 1, wherein the fatty acids comprise:
   a saturated fatty acid of formula: $CH_3(CH_2)_n COOH$, where n is an integer in the range of 4 to 20; and
   an unsaturated fatty acid of formula: $CH_3(CH_2)_m C\!\!=\!\!C(CH_2)_o COOH$, where m and o are independently integer in the range of 2 to 20; or
   salts thereof.

6. The device of claim 1, wherein the balloon is an angioplasty balloon.

7. The device of claim 1, wherein the bioactive agent comprises an antiproliferative agent, an antiinflamatory agent, or an antiplatelet agent.

8. The device of claim 7, wherein the bioactive agent comprises paclitaxel.

9. The device of claim 1, wherein a majority of the nano- or microparticles are non-homogenously distributed in the flexible hydrogel matrix, and partially embedded in the flexible hydrogel matrix at its surface.

10. The device of claim 1, wherein the nano- or microparticles consist of the therapeutic agent.

11. The device of claim 1, wherein about 10% to 100% of the nano- or microparticles associated with the balloon or coating are released from the device upon expansion of the balloon.

12. The device of claim 1, wherein the coating comprising the flexible hydrogel matrix comprises a hydrogel polymer selected from the group consisting of poly(acrylamide), poly(methacrylamide), poly(vinylpyrrolidone), poly(acrylic acid), poly(ethylene glycol), poly(vinyl alcohol), poly(HEMA), methyl vinyl ether/maleic anhydride copolymers, vinyl pyrrolidone/(meth)acrylamide copolymers, and mixture thereof.

13. The device of claim 1, wherein the coating comprising the flexible hydrogel matrix comprises a polymer comprising pendent reacted photogroups that covalently bond the polymer to other polymers in the coating or to a surface of the expandable and collapsible structure.

14. The device of claim 1, wherein the coating comprising the bioactive agent has a thickness of about 5 μm to about 100 μm.

15. The device of claim 1, wherein the nano- or microparticles have an average greatest dimension of about 0.1 μm to about 10 μm.

16. A method of delivering a bioactive agent to a site in a subject, the method comprising:

providing the medical device of claim 1 at a site in a subject; and expanding the balloon at the site in the subject to contact a tissue at the site with the coating comprising the bioactive agent and the lipid coating and to release bioactive agent to the tissue.

17. The device of claim 1, wherein the melting point is in the range of 25° C. to 37° C.

\* \* \* \* \*